US010548738B2

(12) United States Patent
Milz et al.

(10) Patent No.: US 10,548,738 B2
(45) Date of Patent: Feb. 4, 2020

(54) EXPANDABLE INTERBODY IMPLANT

(71) Applicant: Howmedica Osteonics Corp., Mahwah, NJ (US)

(72) Inventors: Bryan D. Milz, Florida, NY (US); Dan Boljonis, Middletown, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 366 days.

(21) Appl. No.: 15/481,854

(22) Filed: Apr. 7, 2017

(65) Prior Publication Data

US 2017/0290671 A1    Oct. 12, 2017

Related U.S. Application Data

(60) Provisional application No. 62/319,513, filed on Apr. 7, 2016.

(51) Int. Cl.
*A61F 2/44*    (2006.01)

(52) U.S. Cl.
CPC ............... *A61F 2/44* (2013.01); *A61F 2/442* (2013.01); *A61F 2/447* (2013.01); *A61F 2/4425* (2013.01);
(Continued)

(58) Field of Classification Search
CPC combination set(s) only.
See application file for complete search history.

(56) References Cited

U.S. PATENT DOCUMENTS 3,875,595 A    4/1975  Froning
4,932,975 A    6/1990  Main et al.
(Continued)

FOREIGN PATENT DOCUMENTS

CN    1756516 A    4/2006
CN    101610741 A    12/2009
(Continued)

OTHER PUBLICATIONS

Extended European Search Report for Application No. EP17165398, dated Aug. 2, 2017.
(Continued)

*Primary Examiner* — Sameh R Boles
(74) *Attorney, Agent, or Firm* — Lerner, David, Littenberg, Krumholz & Mentlik, LLP

(57) ABSTRACT

An expandable interbody implant is expandable from a contracted configuration to an expanded configuration by moving opposing first and second vertebral-engaging surfaces apart from one another. The implant includes a locking system for restraining contraction of the implant. The locking system may have a locked configuration, in which the first and second surfaces are prevented from moving back towards the contracted configuration, and the locking system may have an unlocked configuration, in which the first and second surfaces are permitted to move back towards the contracted configuration. The locking system may be controlled by rotation of one or more pinions. The pinions may, in turn, be controlled by linear movement of a rack. The rack may be configured so as to bias the locking system towards the locked configuration. The implant may also include a stop for constraining the maximum expansion of the implant.

17 Claims, 17 Drawing Sheets

(52) U.S. Cl.
CPC ...... *A61F 2/4455* (2013.01); *A61F 2002/443* (2013.01)

(56) References Cited

U.S. PATENT DOCUMENTS

| | | |
|---|---|---|
| 4,969,888 A | 11/1990 | Scholten et al. |
| 5,236,460 A | 8/1993 | Barber |
| 5,653,763 A | 8/1997 | Errico et al. |
| 5,665,122 A | 9/1997 | Kambin |
| 5,723,013 A | 3/1998 | Jeanson et al. |
| 5,827,328 A | 10/1998 | Buttermann |
| 5,865,848 A | 2/1999 | Baker |
| 5,916,267 A | 6/1999 | Tienboon |
| 5,980,522 A | 11/1999 | Koros et al. |
| 5,989,290 A | 11/1999 | Biedermann et al. |
| 6,039,761 A | 3/2000 | Li et al. |
| 6,102,950 A | 8/2000 | Vaccaro |
| 6,127,597 A | 10/2000 | Beyar et al. |
| 6,176,881 B1 | 1/2001 | Schar et al. |
| 6,193,756 B1 | 2/2001 | Studer et al. |
| 6,214,012 B1 | 4/2001 | Karpman et al. |
| 6,296,665 B1 | 10/2001 | Strnad et al. |
| 6,371,989 B1 | 4/2002 | Chauvin et al. |
| 6,375,682 B1 | 4/2002 | Fleischmann et al. |
| 6,375,683 B1 | 4/2002 | Crozet et al. |
| 6,395,032 B1 | 5/2002 | Gauchet |
| 6,454,806 B1 | 9/2002 | Cohen et al. |
| 6,527,803 B1 | 3/2003 | Crozet et al. |
| 6,562,074 B2 | 5/2003 | Gerbec et al. |
| 6,582,467 B1 | 6/2003 | Teitelbaum et al. |
| 6,585,699 B2 | 7/2003 | Ljunggreen et al. |
| 6,692,495 B1 | 2/2004 | Zacouto |
| 6,719,796 B2 | 4/2004 | Cohen et al. |
| 6,723,126 B1 | 4/2004 | Berry |
| 6,730,088 B2 | 5/2004 | Yeh |
| 6,764,491 B2 | 7/2004 | Frey et al. |
| 6,830,570 B1 | 12/2004 | Frey et al. |
| 6,835,207 B2 | 12/2004 | Zacouto et al. |
| 6,866,682 B1 | 3/2005 | An et al. |
| 6,875,235 B2 | 4/2005 | Ferree |
| 6,953,477 B2 | 10/2005 | Berry |
| 6,960,232 B2 | 11/2005 | Lyons et al. |
| 6,981,989 B1 | 1/2006 | Fleischmann et al. |
| 7,001,431 B2 | 2/2006 | Bao et al. |
| 7,018,415 B1 | 3/2006 | McKay |
| 7,018,416 B2 | 3/2006 | Hanson et al. |
| 7,060,037 B2 | 6/2006 | Lussier et al. |
| 7,060,073 B2 | 6/2006 | Frey et al. |
| 7,066,958 B2 | 6/2006 | Ferree |
| 7,094,257 B2 | 8/2006 | Mujwid et al. |
| 7,166,110 B2 | 1/2007 | Yundt |
| 7,204,853 B2 | 4/2007 | Gordon et al. |
| 7,214,243 B2 | 5/2007 | Taylor |
| 7,217,293 B2 | 5/2007 | Branch, Jr. |
| 7,282,063 B2 | 10/2007 | Cohen et al. |
| 7,291,150 B2 | 11/2007 | Graf |
| 7,291,158 B2 | 11/2007 | Crow et al. |
| 7,316,686 B2 | 1/2008 | Dorchak et al. |
| 7,316,714 B2 | 1/2008 | Gordon et al. |
| 7,351,261 B2 | 4/2008 | Casey |
| 7,407,513 B2 | 8/2008 | Alleyne et al. |
| 7,419,505 B2 | 9/2008 | Fleischmann et al. |
| 7,452,359 B1 | 11/2008 | Michelson |
| 7,470,273 B2 | 12/2008 | Dougherty-Shah |
| 7,481,812 B2 | 1/2009 | Frey et al. |
| 7,485,145 B2 | 2/2009 | Purcell |
| 7,507,241 B2 | 3/2009 | Levy et al. |
| 7,520,900 B2 | 4/2009 | Trieu |
| 7,563,284 B2 | 7/2009 | Coppes et al. |
| 7,563,286 B2 | 7/2009 | Gerber et al. |
| 7,621,956 B2 | 11/2009 | Paul et al. |
| 7,628,815 B2 | 12/2009 | Baumgartner et al. |
| 7,670,359 B2 | 3/2010 | Yundt |
| 7,708,779 B2 | 5/2010 | Edie et al. |
| 7,722,674 B1 | 5/2010 | Grotz |
| 7,731,752 B2 | 6/2010 | Edie et al. |
| 7,731,753 B2 | 6/2010 | Reo et al. |
| 7,771,480 B2 | 8/2010 | Navarro et al. |
| 7,794,501 B2 | 9/2010 | Edie et al. |
| 7,806,935 B2 | 10/2010 | Navarro et al. |
| 7,819,921 B2 | 10/2010 | Grotz |
| 7,824,444 B2 | 11/2010 | Biscup et al. |
| 7,824,445 B2 | 11/2010 | Biro et al. |
| 7,854,766 B2 | 12/2010 | Moskowitz et al. |
| 7,862,618 B2 | 1/2011 | White et al. |
| 7,883,543 B2 | 2/2011 | Sweeney |
| 7,935,124 B2 | 5/2011 | Frey et al. |
| 7,967,863 B2 | 6/2011 | Frey et al. |
| 7,967,867 B2 | 6/2011 | Barreiro et al. |
| 7,985,231 B2 | 7/2011 | Sankaran |
| 7,985,256 B2 | 7/2011 | Grotz et al. |
| 8,021,395 B2 | 9/2011 | Ben-Mokhtar et al. |
| 8,025,680 B2 | 9/2011 | Hayes et al. |
| 8,057,549 B2 | 11/2011 | Butterman et al. |
| 8,062,368 B2 | 11/2011 | Heinz et al. |
| 8,062,373 B2 | 11/2011 | Fabian, Jr. |
| 8,070,813 B2 | 12/2011 | Grotz et al. |
| 8,105,382 B2 | 1/2012 | Olmos et al. |
| 8,137,401 B2 | 3/2012 | Stad et al. |
| 8,153,785 B2 | 4/2012 | Khire et al. |
| 8,187,331 B2 | 5/2012 | Strohkirch, Jr. et al. |
| 8,192,495 B2 | 6/2012 | Simpson et al. |
| 8,267,939 B2 | 9/2012 | Cipoletti et al. |
| 8,273,124 B2 | 9/2012 | Renganath et al. |
| 8,303,663 B2 | 11/2012 | Jimenez et al. |
| 8,353,961 B2 | 1/2013 | McClintock et al. |
| 8,366,777 B2 | 2/2013 | Matthis et al. |
| 8,394,143 B2 | 3/2013 | Grotz et al. |
| 8,435,296 B2 | 5/2013 | Kadaba et al. |
| 8,454,695 B2 | 6/2013 | Grotz et al. |
| 8,480,741 B2 | 7/2013 | Grotz et al. |
| 8,574,297 B2 | 11/2013 | Stad et al. |
| 8,696,751 B2 | 4/2014 | Ashley et al. |
| 8,894,710 B2 | 11/2014 | Simpson et al. |
| 8,900,305 B2 | 12/2014 | Stad et al. |
| 8,956,413 B2 | 2/2015 | Ashley et al. |
| 8,992,620 B2 | 3/2015 | Ashley et al. |
| 9,028,550 B2 | 5/2015 | Shulock et al. |
| 9,814,600 B2 | 11/2017 | Shulock et al. |
| 2001/0056302 A1 | 12/2001 | Boyer et al. |
| 2002/0128716 A1 | 9/2002 | Cohen et al. |
| 2002/0138146 A1 | 9/2002 | Jackson |
| 2002/0151976 A1 | 10/2002 | Foley et al. |
| 2003/0114899 A1 | 6/2003 | Woods et al. |
| 2004/0030346 A1 | 2/2004 | Frey et al. |
| 2004/0088054 A1 | 5/2004 | Berry |
| 2004/0097928 A1 | 5/2004 | Zdeblick et al. |
| 2004/0133273 A1 | 7/2004 | Cox |
| 2004/0153065 A1 | 8/2004 | Lim |
| 2004/0153156 A1 | 8/2004 | Cohen et al. |
| 2004/0186576 A1 | 9/2004 | Biscup et al. |
| 2005/0033437 A1 | 2/2005 | Bao et al. |
| 2005/0043800 A1 | 2/2005 | Paul et al. |
| 2005/0049590 A1 | 3/2005 | Alleyne et al. |
| 2005/0085910 A1 | 4/2005 | Sweeney |
| 2005/0107881 A1 | 5/2005 | Alleyne et al. |
| 2005/0113842 A1 | 5/2005 | Bertagnoli et al. |
| 2005/0197702 A1 | 9/2005 | Coppes et al. |
| 2005/0216084 A1 | 9/2005 | Fleischmann et al. |
| 2005/0229433 A1 | 10/2005 | Cachia |
| 2005/0251260 A1 | 11/2005 | Gerber et al. |
| 2005/0256576 A1 | 11/2005 | Moskowitz et al. |
| 2005/0273169 A1 | 12/2005 | Purcell |
| 2005/0273170 A1 | 12/2005 | Navarro et al. |
| 2005/0273171 A1 | 12/2005 | Gordon et al. |
| 2006/0036259 A1 | 2/2006 | Carl et al. |
| 2006/0085073 A1 | 4/2006 | Raiszadeh |
| 2006/0089719 A1 | 4/2006 | Trieu |
| 2006/0106416 A1 | 5/2006 | Raymond et al. |
| 2006/0116767 A1 | 6/2006 | Magerl et al. |
| 2006/0142860 A1 | 6/2006 | Navarro et al. |
| 2006/0142861 A1 | 6/2006 | Murray |
| 2006/0149377 A1 | 7/2006 | Navarro et al. |
| 2006/0167547 A1 | 7/2006 | Suddaby |

(56) References Cited

U.S. PATENT DOCUMENTS

| | | |
|---|---|---|
| 2006/0200244 A1 | 9/2006 | Assaker |
| 2006/0235426 A1 | 10/2006 | Lim et al. |
| 2006/0235535 A1 | 10/2006 | Ferree et al. |
| 2006/0264968 A1 | 11/2006 | Frey et al. |
| 2007/0050030 A1 | 3/2007 | Kim |
| 2007/0050033 A1 | 3/2007 | Reo et al. |
| 2007/0073395 A1 | 3/2007 | Baumgartner et al. |
| 2007/0093901 A1 | 4/2007 | Grotz et al. |
| 2007/0093903 A1 | 4/2007 | Cheng |
| 2007/0123987 A1 | 5/2007 | Bernstein |
| 2007/0179611 A1 | 8/2007 | DiPoto et al. |
| 2007/0233254 A1 | 10/2007 | Grotz et al. |
| 2007/0255409 A1 | 11/2007 | Dickson et al. |
| 2007/0255413 A1 | 11/2007 | Edie et al. |
| 2007/0255415 A1 | 11/2007 | Edie et al. |
| 2007/0270961 A1 | 11/2007 | Ferguson |
| 2007/0270964 A1 | 11/2007 | Strohkirch et al. |
| 2007/0288092 A1 | 12/2007 | Bambakidis |
| 2008/0021555 A1 | 1/2008 | White et al. |
| 2008/0021556 A1 | 1/2008 | Edie |
| 2008/0058930 A1 | 3/2008 | Edie et al. |
| 2008/0058931 A1 | 3/2008 | White et al. |
| 2008/0065082 A1 | 3/2008 | Chang et al. |
| 2008/0065220 A1 | 3/2008 | Alleyne et al. |
| 2008/0065221 A1 | 3/2008 | Alleyne et al. |
| 2008/0077150 A1 | 3/2008 | Nguyen |
| 2008/0086276 A1 | 4/2008 | Naka et al. |
| 2008/0097441 A1 | 4/2008 | Hayes et al. |
| 2008/0103601 A1 | 5/2008 | Biro et al. |
| 2008/0114467 A1 | 5/2008 | Capote et al. |
| 2008/0140207 A1 | 6/2008 | Olmos et al. |
| 2008/0147193 A1 | 6/2008 | Matthis et al. |
| 2008/0147194 A1 | 6/2008 | Grotz et al. |
| 2008/0161933 A1 | 7/2008 | Grotz et al. |
| 2008/0177387 A1 | 7/2008 | Parimore et al. |
| 2008/0183204 A1 | 7/2008 | Greenhalgh et al. |
| 2008/0215153 A1 | 9/2008 | Butterman et al. |
| 2008/0243251 A1 | 10/2008 | Stad et al. |
| 2008/0281424 A1 | 11/2008 | Parry et al. |
| 2008/0288073 A1 | 11/2008 | Renganath et al. |
| 2008/0300598 A1 | 12/2008 | Barreiro et al. |
| 2009/0005819 A1 | 1/2009 | Ben-Mokhtar et al. |
| 2009/0005874 A1 | 1/2009 | Fleischmann et al. |
| 2009/0018661 A1 | 1/2009 | Kim et al. |
| 2009/0043312 A1 | 2/2009 | Koulisis et al. |
| 2009/0048676 A1 | 2/2009 | Fabian, Jr. |
| 2009/0105836 A1 | 4/2009 | Frey et al. |
| 2009/0171389 A1 | 7/2009 | Sankaran |
| 2009/0204215 A1 | 8/2009 | McClintock et al. |
| 2009/0216331 A1 | 8/2009 | Grotz et al. |
| 2009/0222100 A1 | 9/2009 | Cipoletti et al. |
| 2009/0270987 A1 | 10/2009 | Heinz et al. |
| 2010/0016970 A1 | 1/2010 | Kapitan et al. |
| 2010/0057204 A1 | 3/2010 | Kadaba et al. |
| 2010/0145455 A1 | 6/2010 | Simpson et al. |
| 2010/0145456 A1 | 6/2010 | Simpson et al. |
| 2010/0249930 A1 | 9/2010 | Myers |
| 2010/0286783 A1 | 11/2010 | Lechmann et al. |
| 2011/0130835 A1* | 6/2011 | Ashley ............. A61F 2/442 623/17.11 |
| 2011/0137416 A1 | 6/2011 | Myers |
| 2011/0270398 A1 | 11/2011 | Grotz et al. |
| 2011/0288646 A1 | 11/2011 | Moskowitz et al. |
| 2012/0059469 A1 | 3/2012 | Myers et al. |
| 2012/0116518 A1 | 5/2012 | Grotz et al. |
| 2012/0130387 A1 | 5/2012 | Simpson et al. |
| 2012/0245695 A1 | 9/2012 | Simpson et al. |
| 2012/0283830 A1 | 11/2012 | Myers |
| 2013/0096677 A1 | 4/2013 | Myers et al. |
| 2013/0158669 A1 | 6/2013 | Sungarian et al. |
| 2013/0197642 A1 | 8/2013 | Ernst |
| 2013/0197647 A1 | 8/2013 | Wolters et al. |
| 2013/0197648 A1 | 8/2013 | Boehm et al. |
| 2013/0204368 A1 | 8/2013 | Prevost |
| 2013/0204374 A1 | 8/2013 | Milella, Jr. |
| 2013/0253650 A1 | 9/2013 | Ashley et al. |
| 2014/0018922 A1 | 1/2014 | Marino et al. |
| 2014/0031938 A1 | 1/2014 | Lechmann et al. |
| 2014/0107787 A1 | 4/2014 | Stinchfield et al. |
| 2014/0243983 A1 | 8/2014 | Galea et al. |
| 2015/0148908 A1 | 5/2015 | Marino et al. |
| 2017/0224506 A1 | 8/2017 | Ashley et al. |
| 2018/0064557 A1 | 3/2018 | Shulock et al. |
| 2018/0098860 A1 | 4/2018 | To et al. |
| 2018/0116811 A1 | 5/2018 | Bernard et al. |
| 2018/0125671 A1 | 5/2018 | Bernard et al. |

FOREIGN PATENT DOCUMENTS

| | | |
|---|---|---|
| CN | 101631516 A | 1/2010 |
| CN | 101686860 A | 3/2010 |
| CN | 101686865 A | 3/2010 |
| DE | 3729600 | 3/1989 |
| EP | 1415624 A1 | 5/2004 |
| EP | 1442715 A2 | 8/2004 |
| JP | 001-518824 A | 10/2001 |
| JP | 008-502372 A | 1/2008 |
| WO | 2002009626 A1 | 2/2002 |
| WO | 2003003951 A1 | 1/2003 |
| WO | 2004016205 A2 | 2/2004 |
| WO | 2004016250 A1 | 2/2004 |
| WO | 2006044786 A2 | 4/2006 |
| WO | 2007124078 A2 | 11/2007 |
| WO | 2008011371 A2 | 1/2008 |
| WO | 2008039811 A2 | 4/2008 |
| WO | 2008086276 A2 | 7/2008 |
| WO | 2008112607 A2 | 9/2008 |
| WO | 2008121251 A2 | 10/2008 |
| WO | 2008148210 A1 | 12/2008 |
| WO | 2009033100 A1 | 3/2009 |
| WO | 2009064787 A2 | 5/2009 |
| WO | 2009105182 A1 | 8/2009 |
| WO | 2009114381 A1 | 9/2009 |
| WO | 2010068725 A2 | 6/2010 |
| WO | 2011011609 A2 | 1/2011 |
| WO | 2011150077 A1 | 12/2011 |

OTHER PUBLICATIONS

Extended European Search Report for Application No. 11787340.6 dated Jun. 25, 2014.
Extended European Search Report for Application No. EP14159619 dated Jun. 12, 2014.
International Search Report & Written Opinion for Application No. PCT/US2009/000974 dated Jun. 5, 2009.
International Search Report and Written Opinion dated Jun. 5, 2009 for related PCT/US2009/000974.
International Search Report and Written Opinion dated Apr. 10, 2008, in related International Application No. PCT/US2007/079474.
International Search Report and Written Opinion dated Aug. 13, 2010, in related International Application No. PCT/US2009/067446 filed Dec. 10, 2009.
International Search Report and Written Opinion dated Jun. 30, 2009, in related International Application No. PCT/US2008/003776 filed Mar. 21, 2008.
International Search Report and Written Opinion dated May 6, 2009, in related International Application No. PCT/US2009/000974 filed Feb. 17, 2009.
International Search Report and Written Opinion dated Nov. 11, 2010, in International Application No. PCT/US2010/031247 entitled "Insertion Handle for Implant."
International Search Report and Written Opinion dated Sep. 22, 2011 in related International Application No. PCT/US2011/037929.
Japanese Office Action for Application No. 2013-512209 dated Jan. 27, 2015.

(56) References Cited

OTHER PUBLICATIONS

U.S. Appl. No. 15/480,781, filed Apr. 6, 2017.
U.S. Appl. No. 62/245,004, filed Oct. 22, 2015.
U.S. Appl. No. 62/319,460, filed Apr. 7, 2016.

* cited by examiner

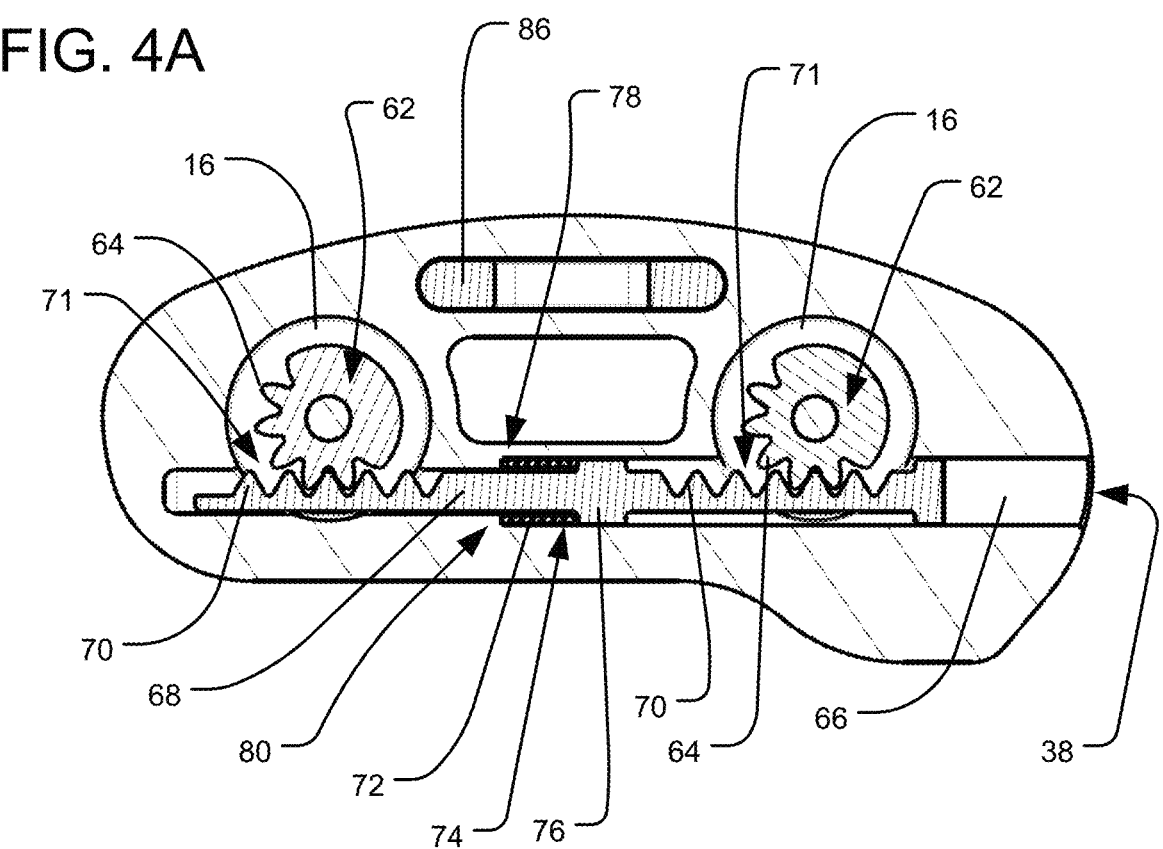
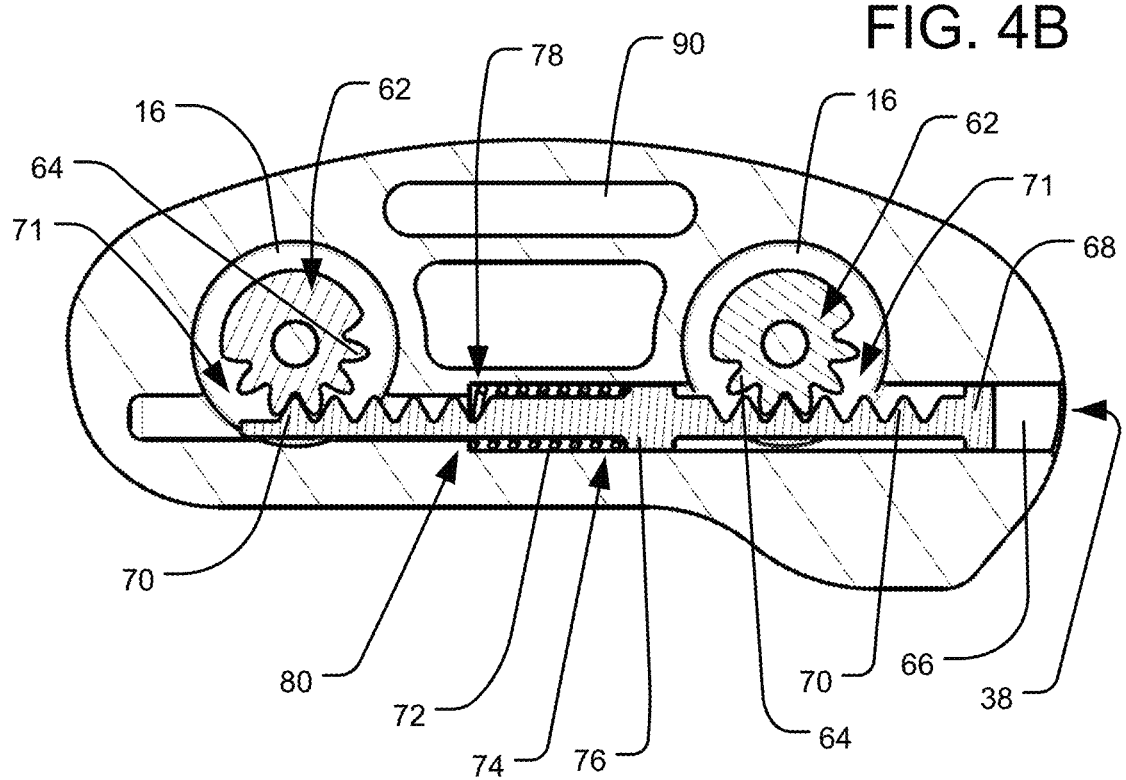

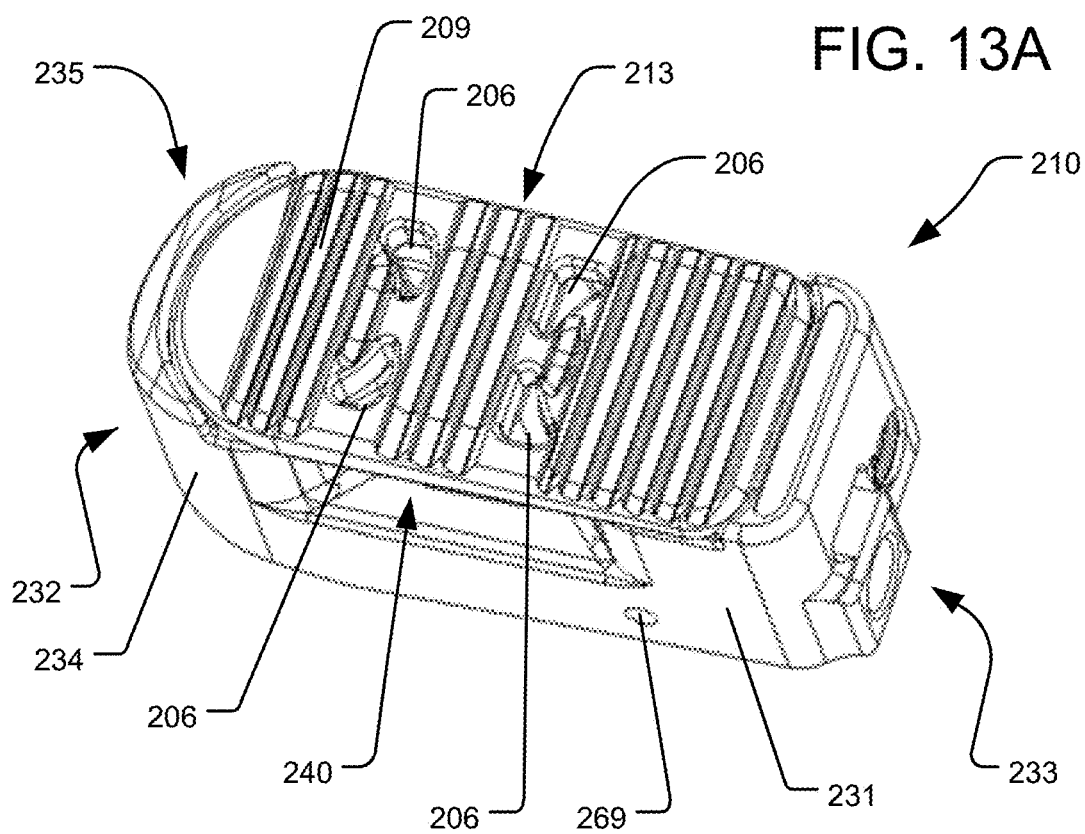
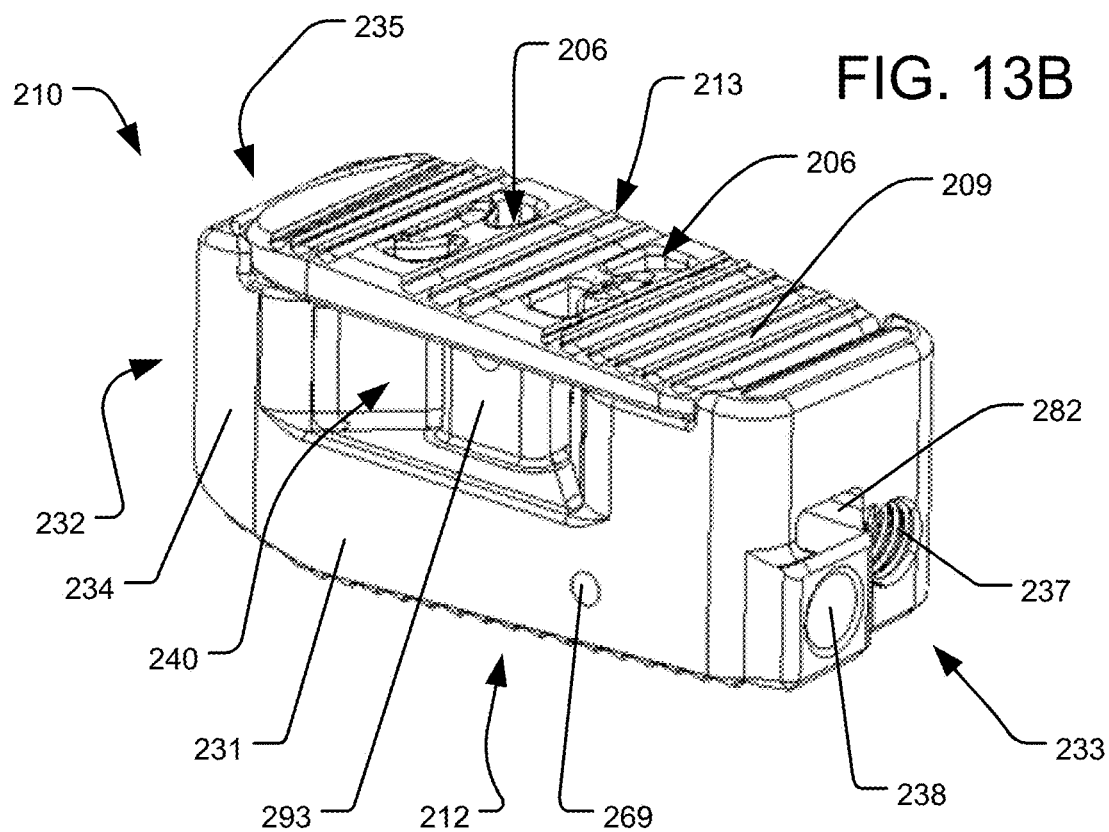

EXPANDABLE INTERBODY IMPLANT

CROSS-REFERENCE TO RELATED APPLICATIONS

This application claims the benefit of the filing date of U.S. Provisional Patent Application No. 62/319,513 filed Apr. 7, 2016, the disclosure of which is hereby incorporated herein by reference.

BACKGROUND OF THE INVENTION

Intervertebral implants are commonly used in spinal surgery, such as in interbody fusion procedures, in which an implant (e.g., a spacer or cage) is placed in the disc space between two vertebrae to be fused together. At least a portion of the disc is typically removed before the implant is positioned in the intervertebral space, and the implant may be supplemented with bone graft material to promote fusion of the vertebrae. Interbody fusion procedures may also be performed in conjunction with other types of fixation, such as pedicle screw fixation, to provide additional stability, particularly while the vertebrae fuse together.

Different interbody fusion procedures can be distinguished by their location along the spine (e.g., in the cervical, thoracic, or lumbar regions); by the type of implant used; and by the surgical approach to the intervertebral space, in which different surgical approaches often imply different structural characteristics of the implant or implants used. Different surgical approaches to the spine include anterior, posterior, and lateral. Examples of interbody fusion techniques performed along a posterior approach include posterior lumbar interbody fusion (PLIF) and transforaminal lumbar interbody fusion (TLIF). PLIF techniques typically include positioning two intervertebral implants into the intervertebral space along a posterior to anterior direction, with one implant being positioned towards the left side of the spine and one implant being positioned towards the right side of the spine. The implants used in such PLIF techniques typically have a straight shape, in that they extend along a central axis. TLIF techniques, by contrast, typically include positioning one intervertebral implant into the intervertebral space (often towards the anterior portion of the intervertebral space) from the posterior of the patient, but the spine is approached on one side from a more lateral position than in PLIF techniques. The implants used in such TLIF techniques are often curved, such that they have an overall kidney bean-like shape.

Included among the different types of intervertebral implants are expandable implants. Such implants often have an initially contracted configuration, such that they have a low profile in the superior-inferior direction, in order to ease insertion into the intervertebral space. Such expandable implants can then be expanded in the superior-inferior direction after implantation, so as to securely engage and stabilize the vertebrae on both sides of the intervertebral space. Examples of such expandable intervertebral implants are disclosed in U.S. Pat. No. 8,992,620 ("the '620 Patent"), which is hereby incorporated by reference herein as if fully set forth herein. Expandable intervertebral implants having certain similar features to those in the '620 Patent are disclosed herein, and therefore some similar nomenclature is used herein for clarity and consistency.

Although considerable effort has been devoted in the art to optimization of such intervertebral systems and methods, still further improvement would be desirable.

BRIEF SUMMARY OF THE INVENTION

The present invention relates to expandable interbody implants, as well as methods of operating the same. Expandable interbody implants in accordance with aspects of the invention include opposing first and second surfaces for engaging respective vertebral bodies on each side of an intervertebral space. When the implants are expanded from a contracted configuration to an expanded configuration, the first and second surfaces are moved apart from one another. A locking system may be provided for restraining contraction of the implant. The locking system may have a locked configuration, in which the first and second surfaces are prevented from moving back towards the contracted configuration, and the locking system may have an unlocked configuration, in which the first and second surfaces are permitted to move back towards the contracted configuration. The locking system may be controlled by rotation of one or more pinions. The pinions may, in turn, be controlled by linear movement of a rack. The rack may be configured so as to bias the locking system towards the locked configuration. Other aspects of the invention may include a stop for constraining the maximum expansion of the implant.

A spinal implant for placement between first and second vertebral bodies, in accordance with an aspect of the invention, includes first and second members having respective first and second surfaces for engaging the respective vertebral bodies. The first and second surfaces may be on opposing sides of the implant to engage the respective vertebral bodies on each side of an intervertebral space. The implant may include at least one extendable support element and a locking system. The extendable support element may have a contracted configuration and at least one extended configuration. The contracted configuration may facilitate deployment of the implant between the first and second vertebral bodies. In the extended configuration, the first and second members may extend away from one another so that the first and second surfaces are positioned further apart from one another than in the contracted configuration. The locking system may comprise at least one locking element movable between a locked configuration and an unlocked configuration. The locking element may prevent movement of the extendable support element towards the contracted configuration when the locking element is in the locked configuration, and the locking element may permit movement of the extendable support element towards the contracted configuration when the locking element is in the unlocked configuration. The locking element may also include a pinion, such that movement of the locking element between the locked and unlocked configuration is actuated by rotation of the pinion.

In accordance with other aspects of the invention, the spinal implant may include a linear rack for rotating the pinion. In accordance with some such aspects of the invention, the linear rack may move linearly within a channel that supplies a fluid for extending the extendable support element. In accordance with other such aspects of the invention, the linear rack may be biased so as to move the locking element towards the locked configuration. For example, the linear rack may be biased by a linear spring.

In accordance with other aspects of the invention, the locking system may further include a second locking element having a second pinion. In accordance with such aspects of the invention, the second locking element may be movable between a locked configuration and an unlocked configuration by rotation of the second pinion. The second locking element may prevent movement of a second one of the extendable support elements towards the contracted configuration when the second locking element is in the locked configuration, and the second locking element may permit movement of the second extendable support element towards the contracted configuration when the second locking element is in the unlocked configuration. A linear rack may be engaged with the pinion and the second pinion for simultaneously rotating the pinion and the second pinion.

In accordance with yet other aspects of the invention, the extendable support element may be configured to be extended by a fluid.

In accordance with other aspects of the invention, the extendable support element may include a piston slidably received within a cylinder. In accordance with some such aspects of the invention, the locking element may be received within the cylinder.

In accordance with other aspects of the invention, the locking system may include a plurality of inter-engaging locking elements, including an upper lock support member and a lower lock support member, and the locking element may be one of the upper and lower lock support members. In accordance with such aspects of the invention, the upper lock support member may have a multi-stepped support surface, and the lower lock support system may have a multi-stepped support surface configured to move into engagement with the multi-stepped support surface of the upper lock support member in the locked configuration. In accordance with some such aspects of the invention, the locking element may be the lower lock support member, which may be rotatable relative to the upper lock support member between the locked and unlocked configurations in response to rotation of the pinion. In accordance with other such aspects of the invention, the lower lock support member may be rotatable relative to the upper lock support member about an axle rigidly connected to one of the first and second members. In accordance with yet other such aspects of the invention, the extendable support element may include a piston slidably received within a cylinder. In accordance with such aspects of the invention, the upper lock support member may be disposed within the piston and the lower lock support member may be rotatably received within the cylinder.

In accordance with other aspects of the invention, one of the first and second members may define a slot extending along an extension direction, and the other of the first and second members may include a projection received within the slot. In accordance with such aspects of the invention, the projection may prevent further extension of the first and second members away from one another when the projection abuts an end of the slot. In accordance with some such aspects of the invention, the extendable support element may comprise a first extendable support element and a second extendable support element, such that the projection and the slot are positioned between the first and second extendable support elements.

In accordance with other aspects of the invention, the implant may have a curved, kidney bean-like shape.

In accordance with yet other aspects of the invention, the implant may have a straight shape along its central longitudinal axis.

A spinal implant for placement between first and second vertebral bodies, in accordance with another aspect of the invention, includes first and second members having respective first and second surfaces for engaging the respective vertebral bodies. The first and second surfaces may be on opposing sides of the implant to engage the respective vertebral bodies on each side of an intervertebral space. The implant may include at least one extendable support element and a locking system. The extendable support element may have a contracted configuration and at least one extended configuration. The contracted configuration may facilitate deployment of the implant between the first and second vertebral bodies. In the extended configuration, the first and second members may extend away from one another along an extension direction so that the first and second surfaces are positioned further apart from one another than in the contracted configuration. One of the first and second members may further define a slot extending along the extension direction, and the other of the first and second members may include a projection received within the slot. The projection desirably prevents further extension of the first and second members away from one another when the projection abuts an end of the slot.

In accordance with another aspect of the above invention, the slot may be defined within the first member and the projection may be provided on the second member. In accordance with such aspect of the invention, the projection may include a pin removably secured within an opening of the second member.

BRIEF DESCRIPTION OF THE DRAWINGS

FIG. 4A is a cross-sectional, plan view of the embodiment of FIG. 1 in a contracted configuration.

FIG. 4B is a cross-sectional, plan view of the embodiment of FIG. 1 in an extended configuration.

FIG. 13A is a perspective view of an embodiment in accordance with another embodiment of the present invention in a contracted configuration.

FIG. 13B is a perspective view of the embodiment of FIG. 13A in a contracted configuration, taken from a different angle.

DETAILED DESCRIPTION

Figure 1:
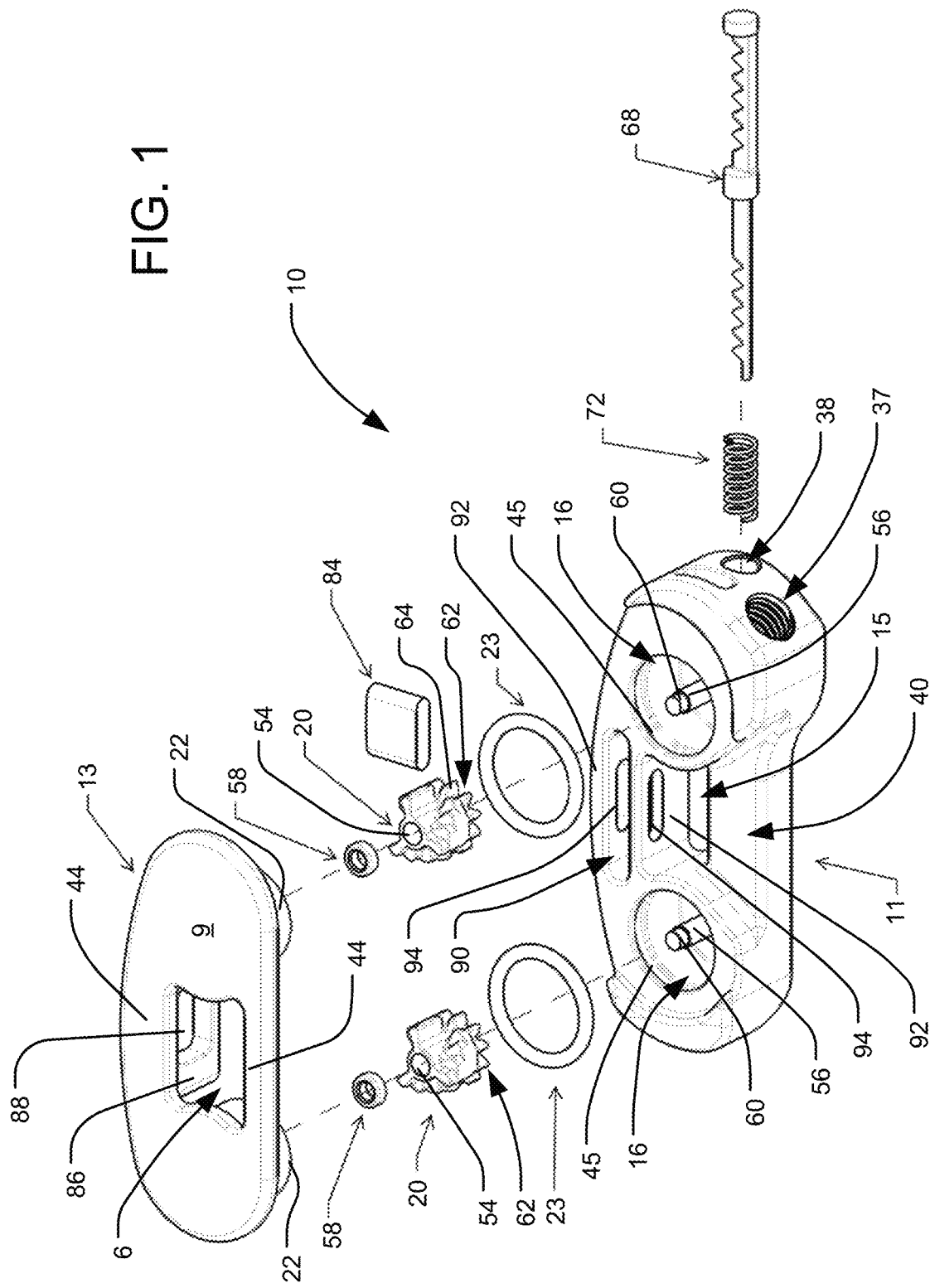
FIG. 1 is an exploded, perspective view of an implant in accordance with one embodiment of the present invention.
Figure 2A:
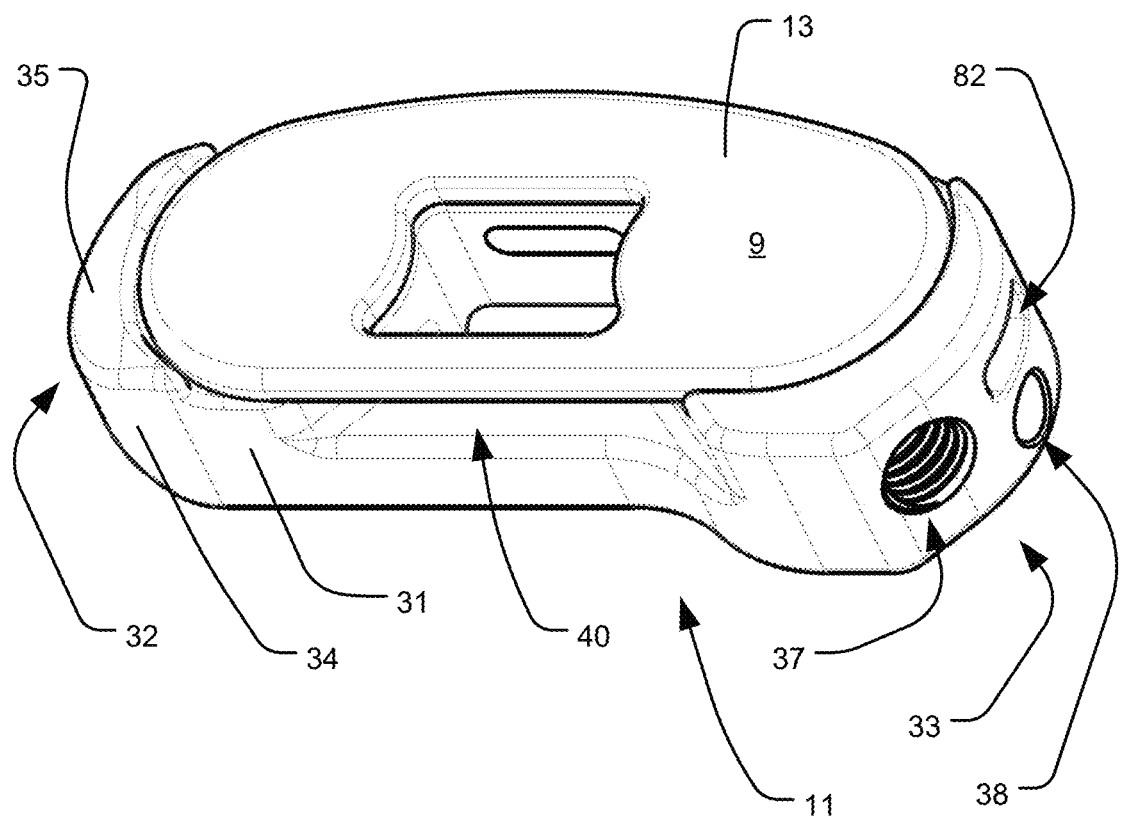
FIG. 2A is a perspective view of the embodiment of FIG. 1 in a contracted configuration.
Figure 2B:
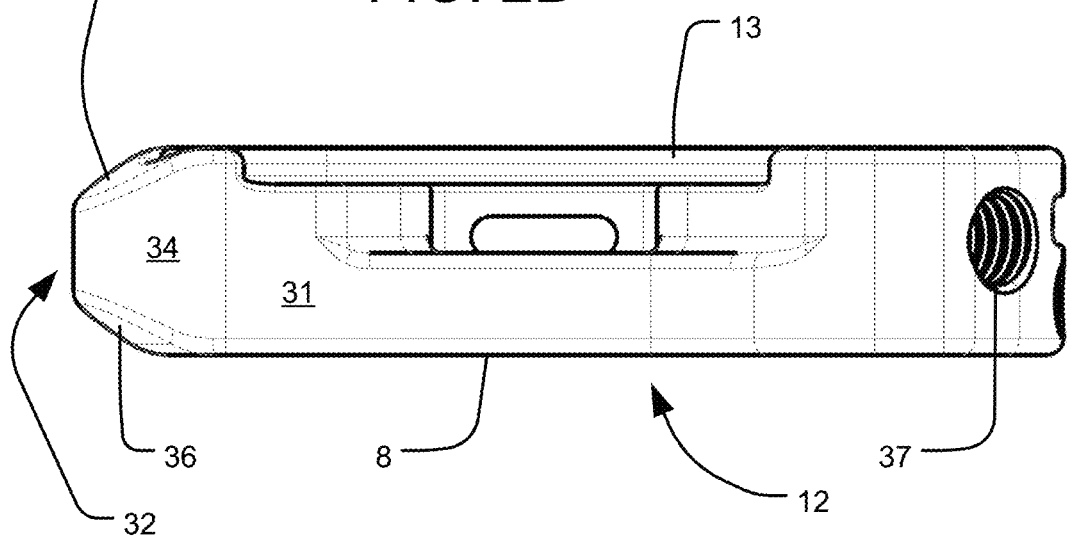
FIG. 2B is a side elevation view of the embodiment of FIG. 1 in a contracted configuration.
Figure 3A:
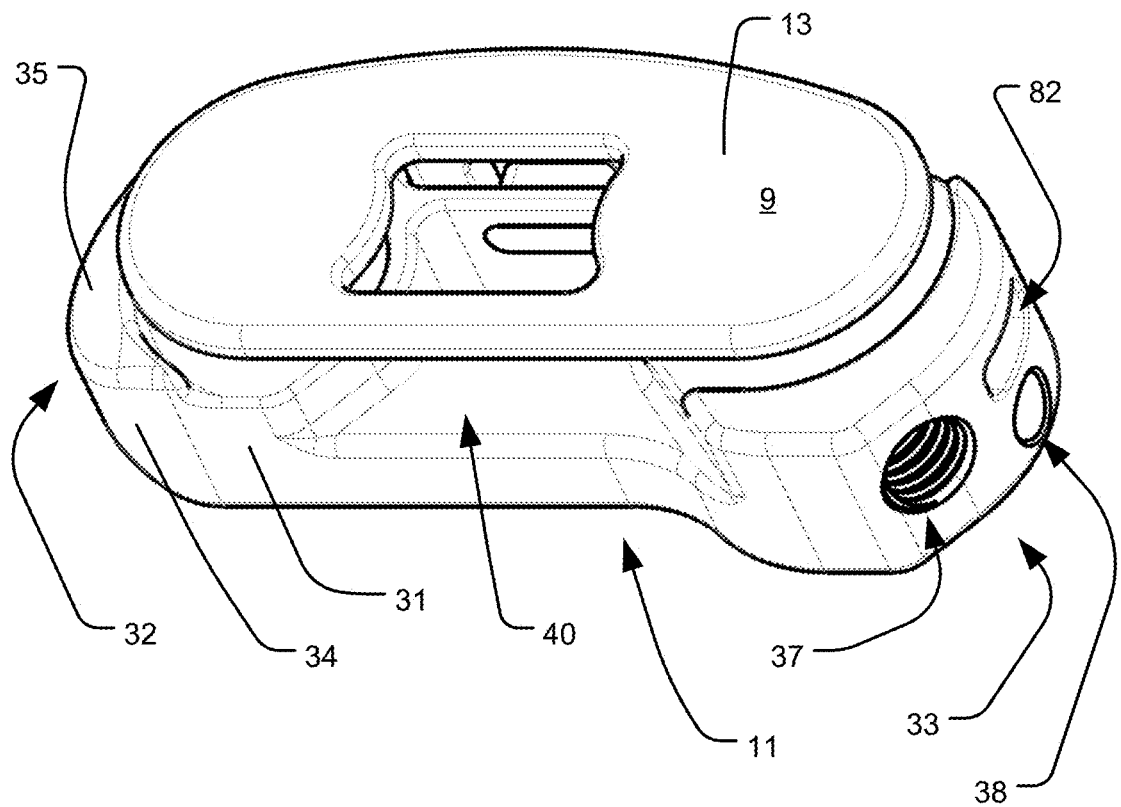
FIG. 3A is a perspective view of the embodiment of FIG. 1 in an extended configuration.
Figure 3B:
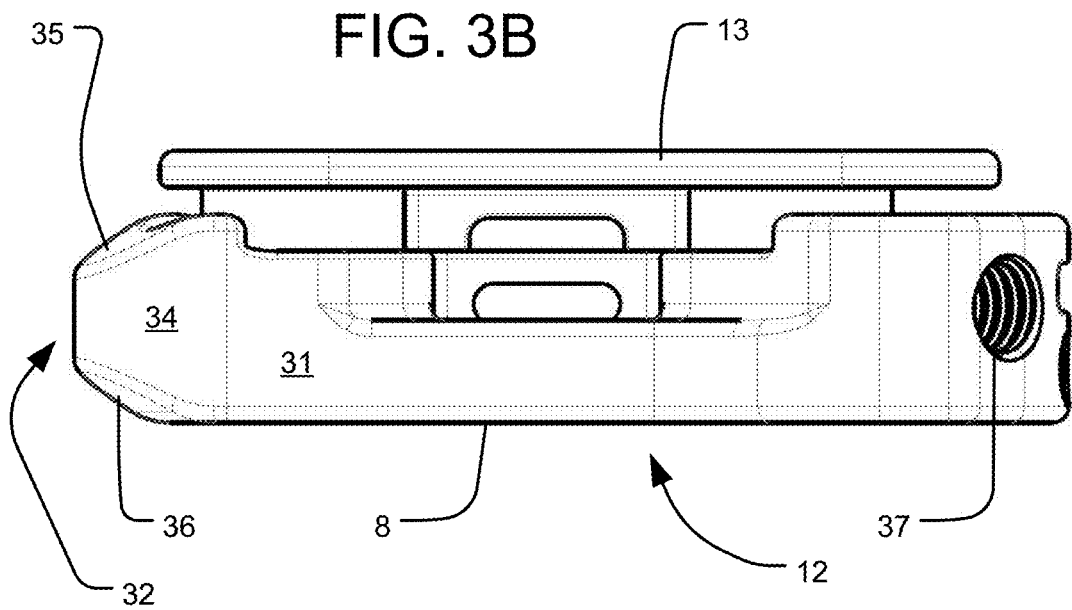
FIG. 3B is a side elevation view of the embodiment of FIG. 1 in an extended configuration.

FIGS. 1-7B illustrate an embodiment of an intervertebral implant 10 in accordance with the present invention. The implant 10 generally includes a housing 11 and a top end plate 13, and the housing 11 defines an interior cavity 15 within it. The top end plate 13 may include an opening 6 within it, bounded by connecting members or struts 44 extending between the left and right sides of the top end plate 13, which opening 6 communicates with the interior cavity 15. Similarly, the bottom 12 of the housing 11 may include one or more openings (not shown) within it, which openings communicate with the interior cavity 15. An example of such an opening 107 in the bottom of the housing is illustrated in the embodiment of the implant 110 illustrated in FIG. 12B. Returning to the embodiment of the implant 10 illustrated in FIGS. 1-7B, the bottom 12 of the housing 11 has a bottom end surface 8 and the top end plate 13 has a top end surface 9. The top end plate 13 is movably connected to the housing 11 on the opposite side of the housing 11 from the bottom end surface 8. The top and bottom end surfaces are the bone engaging surfaces of the implant, for engaging vertebrae above and below the implant when placed in the patient. Moreover, the implant 10 is expandable by translating the top end plate 13 away from the housing 11, from the contracted configuration illustrated in FIGS. 2A-B to the extended configuration illustrated in FIGS. 3A-B.

The implant 10 includes a pair of extendable support elements in the form of pistons 22 attached to the underside of the top end plate 13, which pistons 22 are slidably received within a corresponding pair of cylinders 16 defined within the housing 11. The sliding of the pistons 22 along the cylinders 16 results in the translation of the top end plate 13 so as to expand the implant 10, as discussed above. The pistons 22 and cylinders 16 may operate as part of a hydraulic system, in which the sliding of the pistons 22 away from the bottoms of the cylinders is driven by pressurized fluid within the cylinders 16, as discussed below and in the '620 Patent. Seal members 23, which may be in the form of o-rings, are positioned so as to seal the sliding interface between the cylinders 16 and the respective pistons 22, in order to prevent the pressurized fluid from escaping through that interface. The seal members 23 may be seated within corresponding grooves 45 defined in the outer surfaces of the cylinders 16. In an alternative (not shown), the seal members 23 may be mounted on the pistons 22 so that the seal members 23 slide with the pistons 22 within the cylinders 16, as disclosed in certain embodiments of the '620 Patent.

Figure 6:
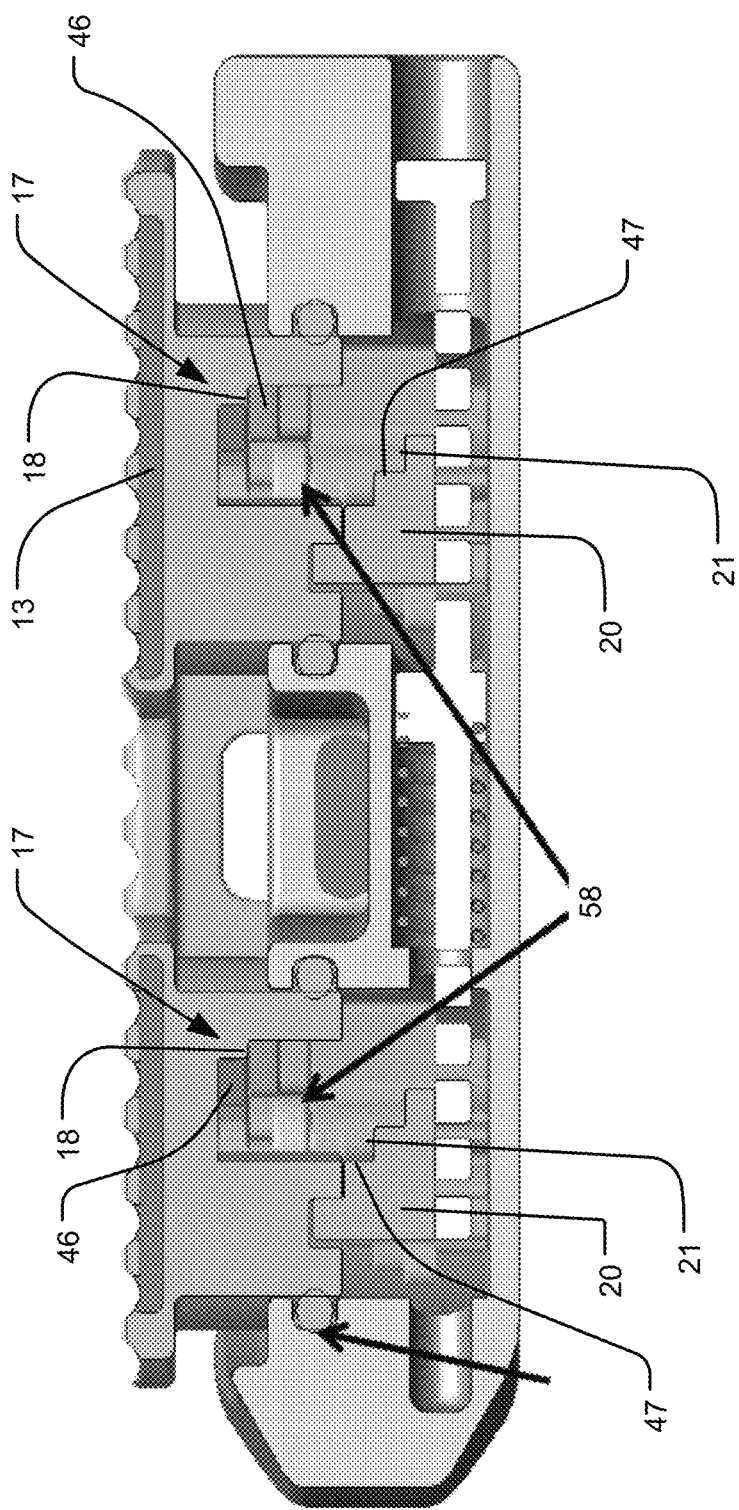
FIG. 6 is a cross-sectional, side elevation view of the embodiment of FIG. 1, showing different features of the implant.

The implant 10 also includes a locking system to lock the position of the top end plate 13 by preventing the top end plate 13 from translating back towards the housing 11. That locking system may include multiple inter-engaging locking elements. For example, the implant 10 may include a pair of lower lock supports 20 positioned within the housing 11 and a corresponding pair of upper lock supports 17 (see FIG. 6) connected to the underside of the top end plate 13. As shown in FIG. 6, the upper lock supports 17 may be positioned within the respective pistons 22, and they may be fixed with respect to the pistons 22 and the top end plate 13. Indeed, each of the upper lock supports 17 may be integrally formed with either or both of the top end plate 13 and the respective piston 22. The upper lock supports 17 have tiered, multi-stepped lower support surfaces 18 and vertical risers or alignment faces 46, much like an inverted spiral staircase. The lower lock supports 20, which may be positioned within the respective pistons 22, similarly have tiered, multi-stepped upper support surfaces 21 and vertical risers or alignment faces 47, much like an upright spiral staircase. The support surfaces 18 of the upper lock supports 17 engage the support surfaces 21 of the lower lock supports 20, and the alignment faces 46 of the upper lock supports are configured to engage the alignment faces 47 of the lower lock supports 20. Thus, the stepped support surfaces of both the upper and lower lock supports form locking surfaces of the locking elements. That is, the engagement of the multi-stepped lower support surfaces 18 of the upper lock supports 17 with the multi-stepped upper support surfaces 21 of the lower lock supports 20 prevents the top end plate 13 from translating back towards the housing 11, as discussed in more detail below and in the '620 Patent.

The tiered, multiple steps of the upper and lower lock supports allow the implant 10 to be locked at several different expanded heights. The underside of the stepped support surfaces 18 of the upper lock support 17 may be provided with increasing riser height (alignment faces 46) in the upward direction to provide smaller incremental expansion near the end of the piston expansion. In addition or alternatively, the stepped support surfaces 21 of the lower lock support 20 may be provided with decreasing riser height in the upward direction for the same reason. A variety of riser heights of the upper lock support 17 or lower lock support 20 can be provided. For example, in one exemplary embodiment, the riser heights may vary in multiples of 0.5 mm to 1.5 mm. The lowermost stepped support surfaces 18 of the upper lock support 17 and the uppermost stepped support surfaces 21 of the lower lock support 20 may also be provided with various lengths and widths. For example, at higher levels of expansion, fewer support surfaces 18, 21 of the respective upper and lower lock supports 17, 20 will be in engagement, and therefore those support surfaces can have increased widths in order to provide sufficient supporting material.

Each lower lock support 20 includes an axial receptacle 54 for receiving and rotating around a respective axle 56 mounted within one of the cylinders 16, which axles 56 may be attached to a bottom portion of the housing 11 (e.g., by being integrally formed with the housing). Bushings 58 may be received within respective grooves 60 towards the top ends of the axles 56, in order to constrain the axial positions of the lower lock supports 20 with respect to the axles 56. The lower lock supports 20 also each include a pinion 62 having teeth 64, such that rotation of the lower lock supports 20 about the axles 56 may be controlled via the application of rotational force to the pinion 62.

As shown in the plan, cross-sectional views of the implant 10 illustrated in FIGS. 4A-B, the implant housing 11 may include a channel 66 formed within it for receiving a rack 68 having teeth 70, such that the rack 68 can translated back and forth within the channel 66. The channel 66 communicates with the cylinders 16 via respective openings 71. The rack 68 is arranged such that its teeth 70 engage with the teeth 64 of the pinions 62 of each lower lock support 20 positioned within the cylinders 16 via those openings 71. In that way, the rotational position of the lower lock supports 20 can be controlled by the translational position of the rack 68 within the channel 66. The rack 68 may be biased in a particular direction by a linear spring 72. In particular, the rack 68 may be biased by the spring 72 in such a way that the lower lock supports 20 are biased towards a locking configuration. The spring 72 may have a rack engagement end 74 for engaging a shoulder 76 of the rack 68, and the spring 72 may have an opposite anchoring end 78 for engaging a transverse face 80 within the channel 66, which face 80 may be defined by a reduction in the diameter of the channel 66.

The housing 11 of the implant 10 comprises an outer wall 31 having a distal end defining a leading nose 32 and a proximal end defining an engagement region 33. The leading nose 32 has inwardly directed side tapered faces 34 and a top tapered face 35 and bottom tapered face 36. These tapered faces 34, 35, and 36 enable non-traumatic insertion of the implant 10 past neural elements and between vertebral bodies. The distal end may also include structures that aid in manipulating the implant in situ (e.g., steering elements that facilitate at least partial rotation of the implant). The engagement region 33 includes a delivery tool anchor 37, which allows secure attachment of the implant 10 to a delivery tool (not shown), such as one illustrated in U.S. Pat. Nos. 8,070,813; 8,998,924; 9,028,550; U.S. Provisional Patent Application No. 62/319,460 filed on Apr. 7, 2016 (hereinafter "the '460 Provisional"); or U.S. patent application Ser. No. 15/480,781 filed on Apr. 6, 2017, the disclosures of all of which are hereby incorporated by reference herein as if fully set forth herein. The engagement region 33 also contains one or more pressure input ports 38, which are used to deliver a pressurized fluid to the interiors of cylinders 16 in order to expand the implant 10. For example, as disclosed in the '460 Provisional, the pressure input port(s) 38 may receive a tube set in sealing engagement, or may sealingly engage a sealing aperture around the edge of the pressure input port 38, so that the pressurized fluid (e.g., saline) may be provided thereby into the pressure input port 38. The engagement region 33 may also include one or more engagement features, such as a recess 82, which may be engageable by the delivery tool in order to act as an anti-rotation feature for securing the rotational orientation of the implant 10 with respect to the delivery tool anchor 37, as also disclosed in the '460 Provisional. The outer wall 31 of the housing 11 also provides one or more side openings 40, which provide space for bony ingrowth into the central cavity 15 in the housing 11 and may also provide radiolucent openings for the radiographic imaging of the process of bony ingrowth.

As shown in FIGS. 4A-B, the channel 66 containing the rack 68 may also serve as a pressure channel for delivering the pressurized fluid from the pressure input port 38 to the interior of cylinders 16 via the openings 71. In an alternative embodiment (not shown), the pressure input port 38 may be a distinct opening in the housing 11 from that communicating with the channel 66. In such an embodiment, separate pressure channels (not shown) may alternatively or additionally deliver the pressurized fluid from the pressure input port 38 to the interior of the cylinders 16, as shown in certain embodiments of the '620 Patent.

Implant 10 is configured to be implanted between opposing vertebral bodies in the spine to facilitate bony fusion between those vertebral bodies. The implant 10 is shown in its collapsed or contracted configuration in FIGS. 2A-B and in one example of its expanded configuration in FIGS. 3A-B. In the collapsed state, the implant 10 can be inserted easily into the intervertebral body space through a minimal incision and with minimal tissue removal. Once in that space, the implant 10 can be expanded against the two opposing vertebral bodies to distract them and thereby restore height to the intervertebral space. This provides stable opposition of the implant 10 to both vertebral bodies and optimizes the bony fusion process. The fusion process can also be enhanced by filling the interior cavity 15 with autologous and/or allogeneic bone graft, a bone growth enabling matrix, and/or bone growth stimulating substances prior to and/or after insertion into the body.

Figure 7A:
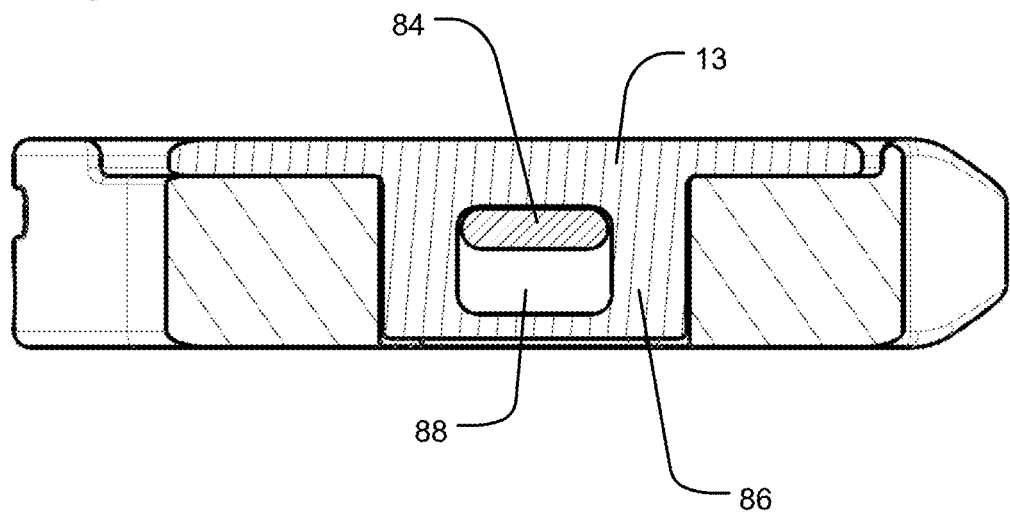
FIG. 7A is a cross-sectional, side elevation view of the embodiment of FIG. 1 in a contracted configuration.
Figure 7B:
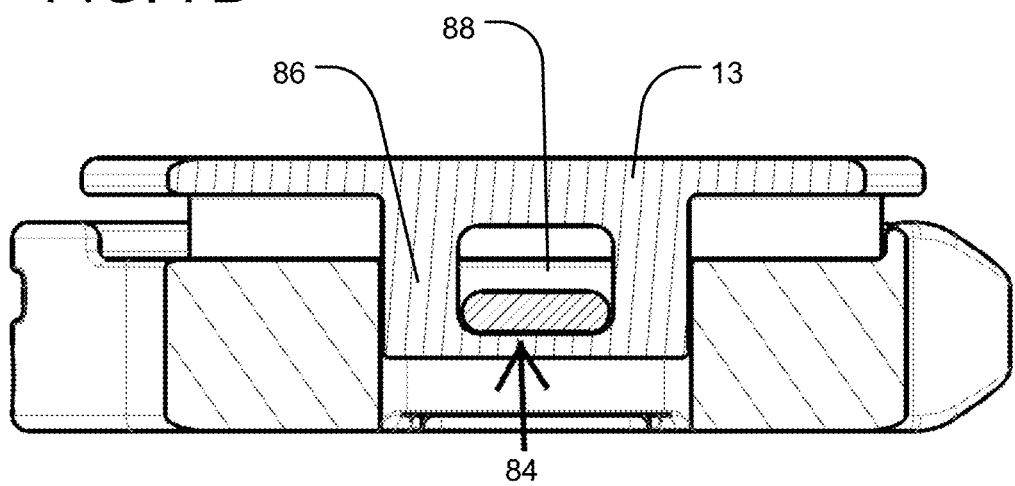
FIG. 7B is a cross-sectional, side elevation view of the embodiment of FIG. 1 in an extended configuration.

As shown in FIG. 1, the implant 10 may include a stop pin 84 (which may be removable) to constrain the maximum extension of the top end plate 13. Specifically, the top end plate 13 may include a distally extending projection 86 having a slot 88 defined within it, which projection 86 may be received within a space 90 defined within the housing 11. That space may be defined between two walls 92, although only one wall 92 may be provided in an alternative embodiment. Each wall 92 may include a pin opening 94, such that the stop pin 84 may be received within one or both openings 94, and, in traversing the space 90, the stop pin 84 may pass through the slot 88 in the projection 86 of the top end plate 13. Thus, the stop pin 84 will limit the extension of the top end plate 13 by preventing the top end plate from translating further once the bottom of the slot 88 in the distally extending projection 86 engages the pin 84, as shown in FIGS. 7A-B. That is, in moving from the contracted configuration of FIG. 7A to the extended configuration of FIG. 7B, the bottom of the slot 88 comes into contact with the pin 84, which prevents further movement of the top end plate 13 away from the housing 11. Additionally, or alternatively, the uppermost support surface of the lower lock support 20 may have a lock support stop (not shown) which engages the lowermost alignment faces 46 of the upper lock support, in order to prevent the lower lock support 20 from over rotating as it engages the upper lock support 17, as disclosed in the '620 Patent.

In operation, upon the extension of the top end plate 13 and the attached upper lock supports 17, the lower lock supports 20 rotate about the cylinders 16 due to the force applied by the rack 68 from the linear spring 72. Thus, the alignment faces 47 of the lower lock supports 20 are forced against the alignment faces 46 of the upper lock support 17. When the cylinders 16 are pressurized, the pistons 22 raise the top end plate 13 and attached upper lock supports 17, thus lifting the support surfaces 18 of the upper lock support 17 off of the support surfaces 21 of the lower lock support 20, and also moving the lower alignment faces 46 past the upper alignment faces 47. When the alignment faces 46 of the upper lock support 17 have cleared the alignment faces 47 of the lower lock support 20, the locking actuator (i.e., linear spring 72), which is engaging the rack 68 meshed with the teeth 64 of the pinions 62 of each lower lock support 20, forces the lower lock supports 20 to rotate. The support surfaces 21 of the rotating lower lock supports 20 then move to the next lower level of the support surfaces 18 of the raised upper lock supports 17 until the alignment faces 47 of the lower lock supports 20 engage the next level of the alignment faces 46 of the upper lock supports 17. The lower lock support 20 and upper lock support 17 thus lock the top end plate 13 at this expanded level. This process repeats itself at each locking level.

Figure 5A:
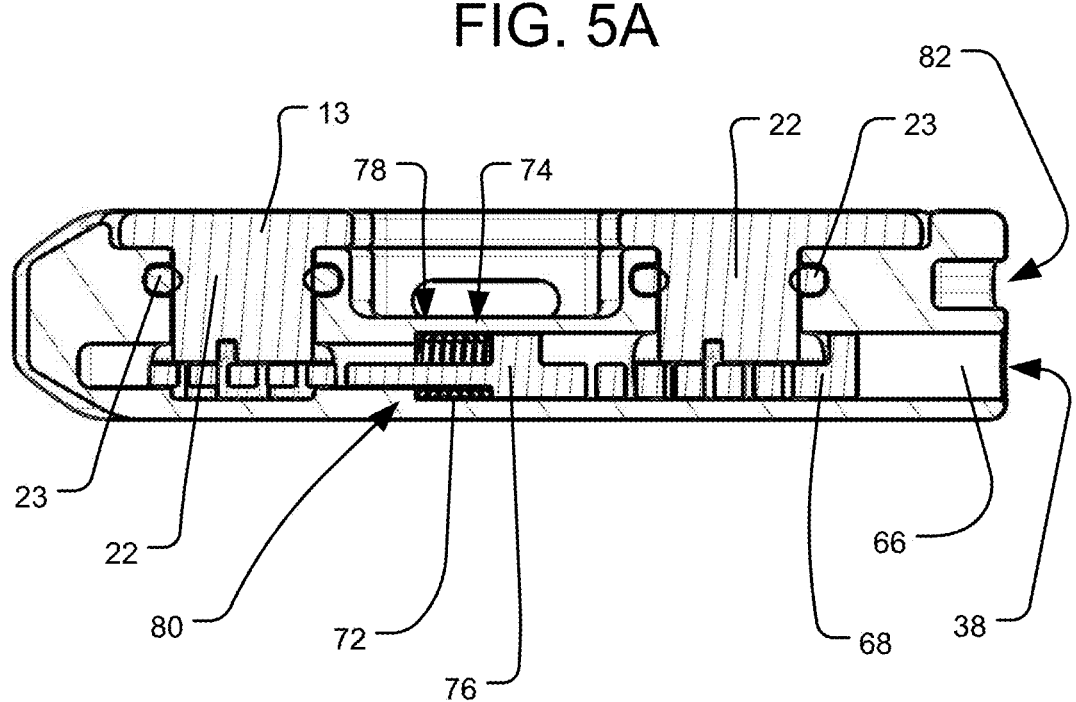
FIG. 5A is a cross-sectional, side elevation view of the embodiment of FIG. 1 in a contracted configuration.
Figure 5B:
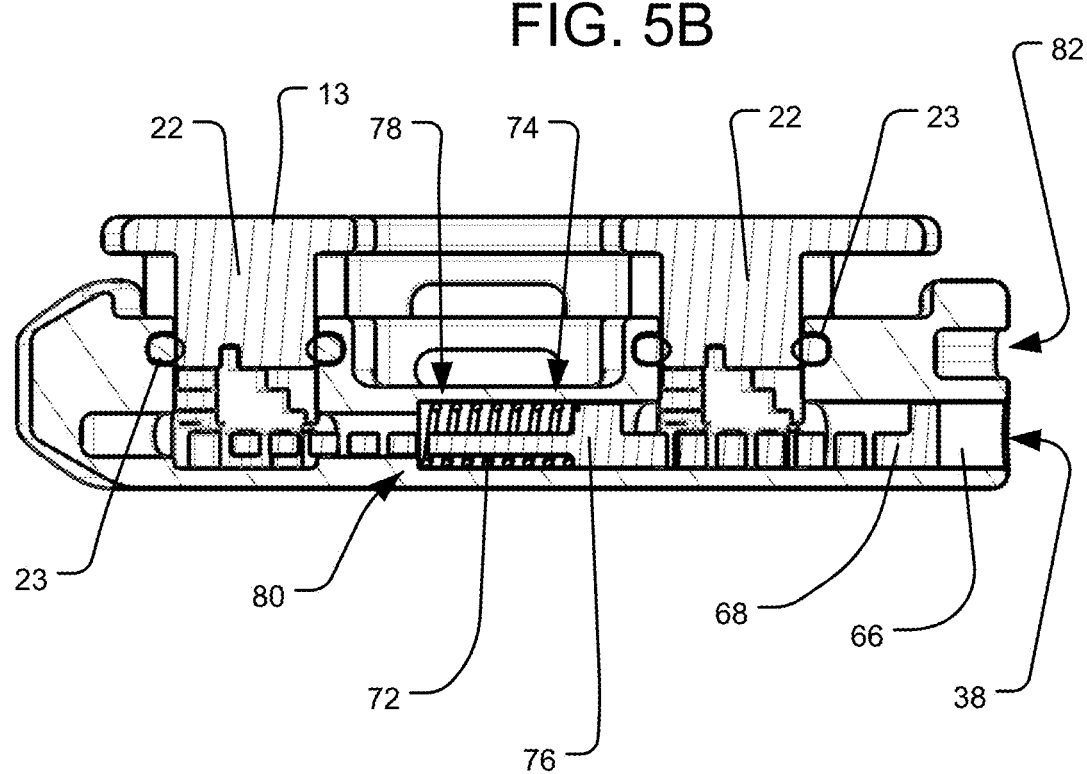
FIG. 5B is a cross-sectional, side elevation view of the embodiment of FIG. 1 in an extended configuration.

The above-described operation of the locking components is illustrated in FIGS. 4A-B and 5A-B. Specifically, FIG. 4A illustrates the configuration of the locking components when the implant 10 is in the contracted configuration (see FIGS. 2A-B), in which the rack 68 is positioned at its distal-most position within the channel 66 (i.e., the left-most position in FIG. 4A), such that the spring 72 is compressed. FIG. 4B illustrates the configuration of the locking components when the implant 10 is in an extended configuration (see FIGS. 3A-B). As shown in the figures, in moving to the extended configuration of FIG. 4B, the spring 72 has become less compressed and it has pushed the rack 68 towards the right, away from the distal end of the channel 66, which has caused the pinions 62 of the lower lock supports 20 to rotate counterclockwise. FIGS. 5A and 5B also illustrate the movement of the locking components in transitioning between the contracted configuration illustrated in FIG. 5A and the extended configuration illustrated in FIG. 5B. As shown in FIG. 5B, the pistons 22 are advanced to a higher position along the lower lock supports 20.

The implant 10 may also be unlocked, to allow the top end plate 13 to move back towards the housing 11. Specifically, the rack 68 can be depressed by pushing it towards the distal end of the housing 11, for example with a component (e.g., a relatively rigid wire) inserted into the open end of the channel 66 (i.e., into the pressure input port 38, in the illustrated embodiment), which will cause the lower lock supports 20 to rotate out of engagement with the upper lock supports 17 and allow the implant 10 to collapse.

Some benefits believed to be provided by the rack-and-pinion design of the locking components disclosed herein include the tangential arrangement of the rack 68 with respect to the pinions 62 (whereby the force applied to the pinions 62 is always at a constant distance from the center of rotation of the pinions 62), which results in a consistent amount of moment being applied to both lower lock supports 20, regardless of the rotational orientation of the lower lock supports. The use of a single linear spring 72 to bias the single rack 68, which drives the pinions 62 of both lower lock supports 20, also allows for the moment load to be applied equally to both lower lock supports. The design of the locking components disclosed herein also allows for both lower lock supports 20 to have identical structures, which simplifies manufacturability and assembly of those components. Indeed, overall benefits of the present design are believed to include a minimal use of different subcomponents, which results in ease of manufacturing and assembly, as well as improved ease of use and reliability (particularly with regard to unlocking the implant so as to allow it to collapse from its extended configuration).

Another embodiment of an intervertebral implant 110 in accordance with the present invention is illustrated in FIGS. 8-12B. Unless otherwise noted, the components of the embodiment of FIGS. 8-12B are similar to those of the embodiment illustrated in FIGS. 1-7B. Moreover, reference numerals in FIGS. 8-12B similar to those in FIGS. 1-7B (i.e., increased by 100) are used to refer to analogous elements, and therefore such analogous elements may not be separately discussed below in connection with the embodiment of FIGS. 8-12B. The principal differences between the embodiment of the implant 110 in FIGS. 8-12B and the embodiment of the implant 10 in FIGS. 1-7B are discussed below.

Figure 8:
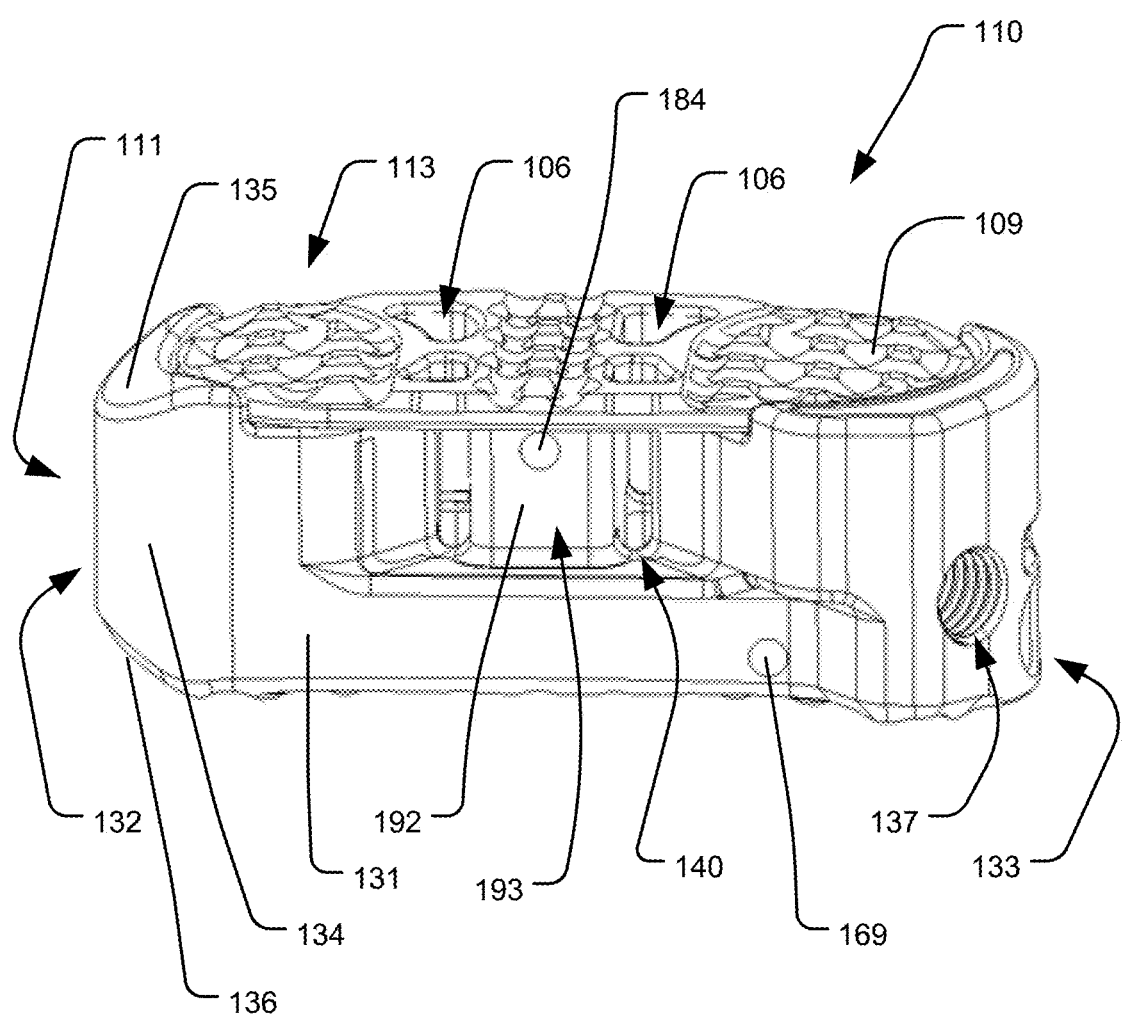
FIG. 8 is a perspective view of an embodiment in accordance with another embodiment of the present invention in a contracted configuration.
Figure 9:
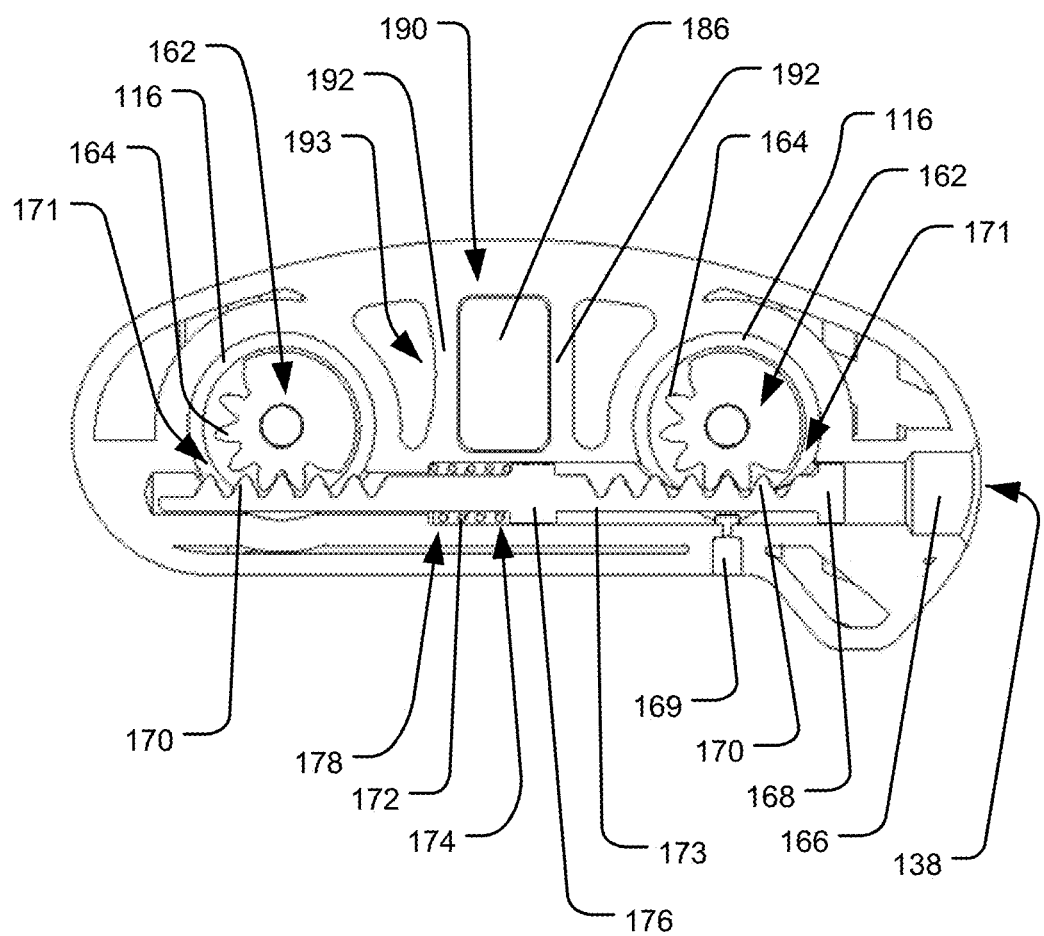
FIG. 9 is a cross-sectional, plan view of the embodiment of FIG. 8.

The distally extending projection 186 from the top end plate 113, which is received within a space 190 defined within the housing 111, has a different geometry and location in the embodiment of FIGS. 8-12B than the projection 86 of the embodiment of FIGS. 1-7B. For example, rather than having a long, thin, generally planar profile that extends longitudinally along one side of the implant 10 (i.e., the anterior side), as shown in FIGS. 4A-B, the projection 186 of the implant 110 is more rectangular, with its longer dimension extending across the width of the implant 110 in the anterior/posterior direction. As shown in FIG. 9, the projection 186 is received within a rectangular space 190 defined within a rectangular box 193 having two longer walls 192 that extend in the anterior/posterior direction across the width of the implant 110. Preferably, the geometry of the projection 186 is such that at least a portion of the projection extends across a longitudinal axis defined between the centers of the cylinders 116. In that way, the interaction of the projection 186 within the space 190 of the box 193 provides more stability to the top end plate 113 than the embodiment 10. That is, by having the projection 186 more centrally located between the cylinders 116 and pistons 122, rather than off to one side (i.e., the anterior side), the top end plate 113 is less likely to be torqued about the longitudinal axis of the implant 110 when the stop pin 184 acts on the projection 186 in limiting the maximum expansion.

Figure 10:
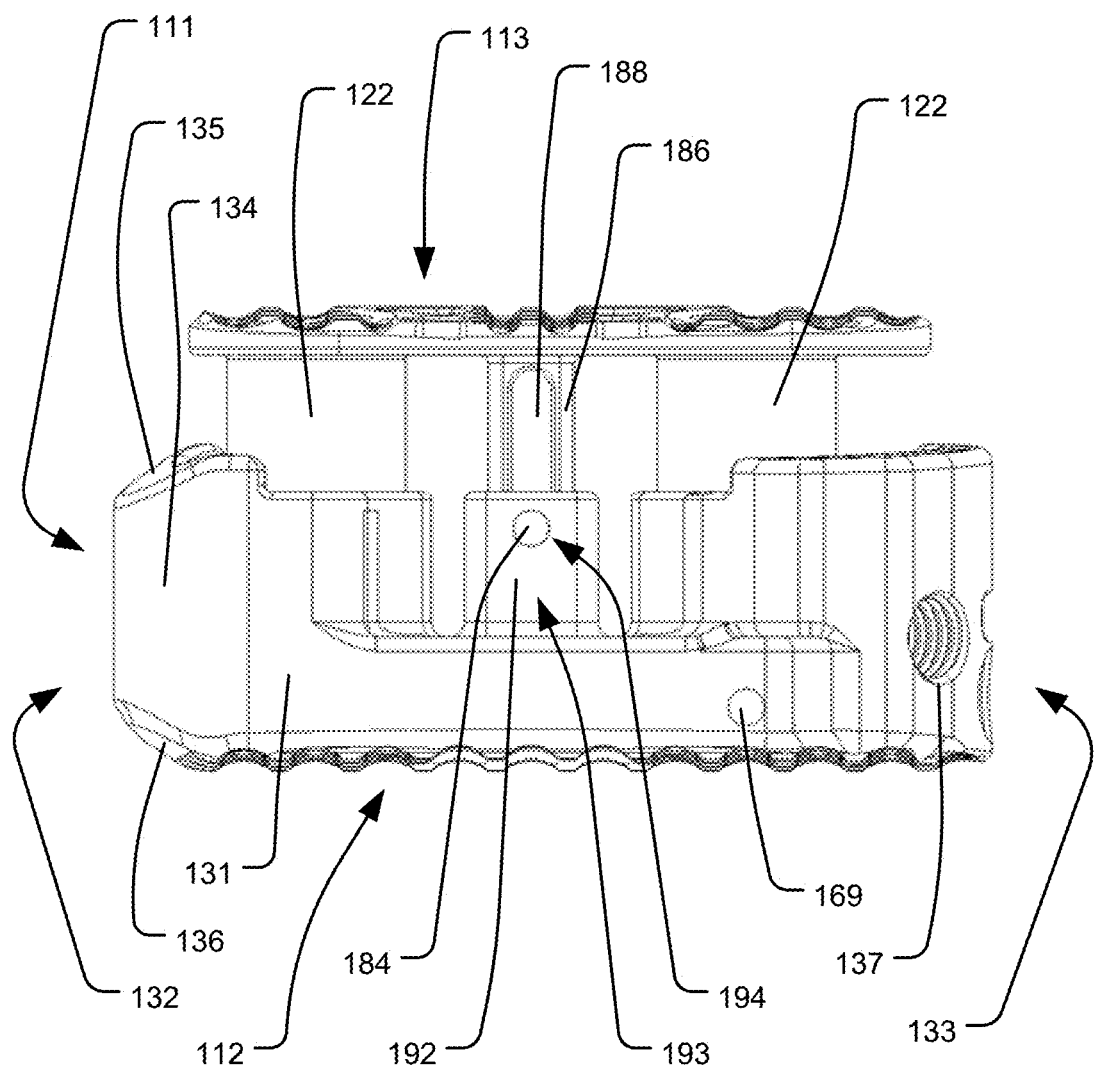
FIG. 10 is a side elevation view of the embodiment of FIG. 8 in an extended configuration.
Figure 12A:
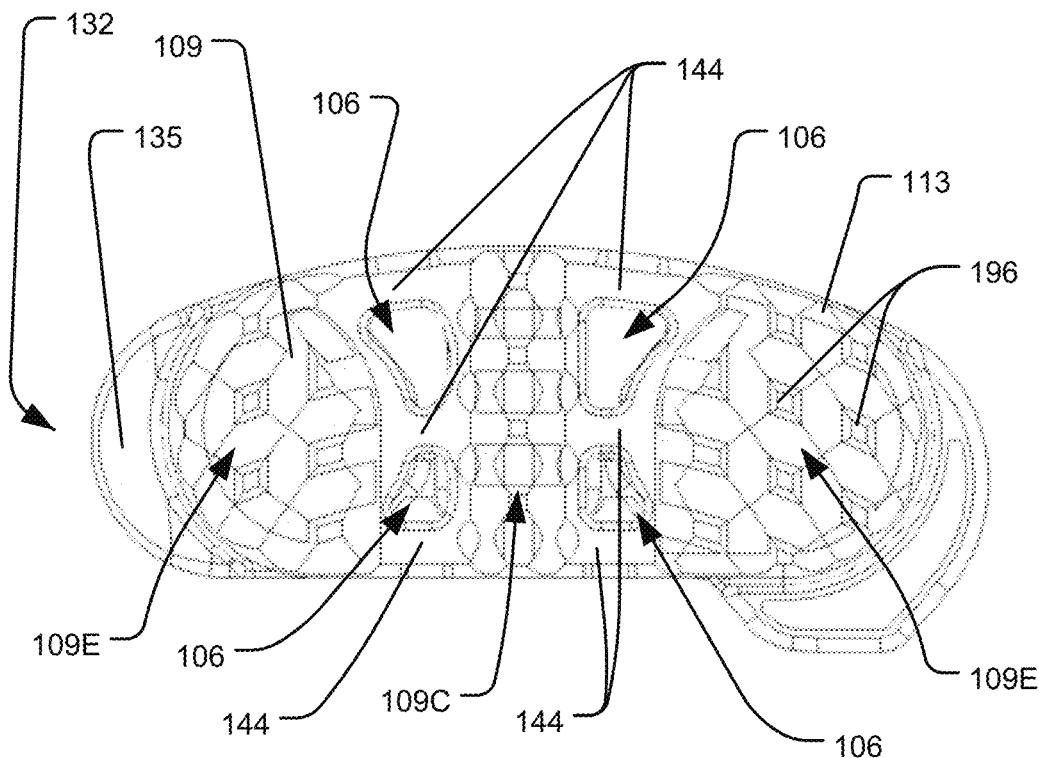
FIG. 12A is a top plan view of the embodiment of FIG. 8.
Figure 12B:
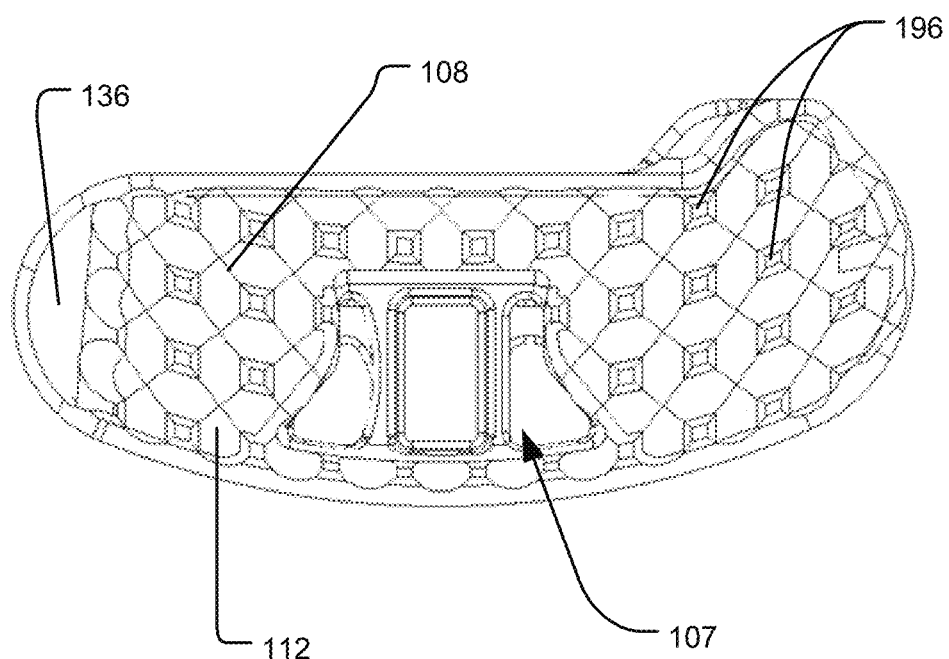
FIG. 12B is a bottom plan view of the embodiment of FIG. 8.
Figure 14:
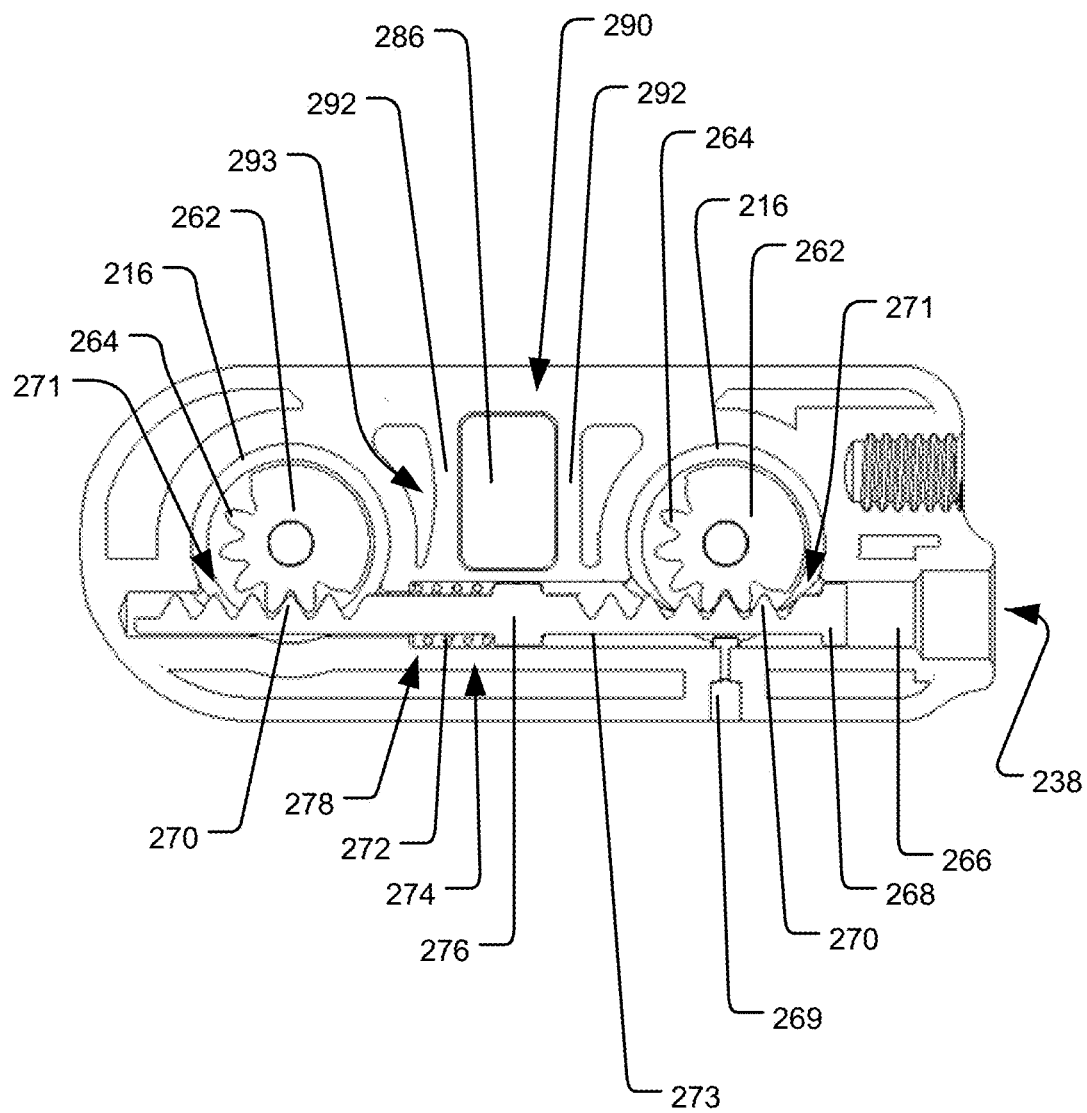
FIG. 14 is a cross-sectional, plan view of the embodiment of FIG. 13A.

As shown in FIGS. 8 and 10, the stop pin 184 may have a more cylindrical configuration than the stop pin 84 of the implant 10, and the pin opening 194 in the box 193 as well as the slot 188 in the projection 186 that receives the stop pin 184, may be shaped accordingly. Additionally, by changing the geometry of the projection 186 and centering it between the pistons 122, the opening in the top end plate 113 may be reconfigured. In particular, as shown in FIG. 12A, the centrally-located projection 186 may result in a central portion 109C of the top end surface 109 of the top end plate 113. Thus, the opening in the top end plate 113 may be subdivided into multiple openings 106 by the central portion 109C and multiple struts 144 that connect the central portion 109C to the end portions 109E of the top end plate 113. Such struts 144 desirably provide stiffness and strength to the top end plate 113, so as to transfer the stopping force from the projection 186 to the rest of the top end plate 113.

As shown in FIG. 9, the implant 110 may include an anti-rotation pin 169 received within a bore in the housing 111 that communicates with the channel 166. In that way, the distal end of the anti-rotation pin 169 desirably abuts a flat side 173 along the back of the rack 168, so as to constrain the rotational orientation of the rack 168 about its longitudinal axis while the rack 168 translates along the channel 166. That is, by positioning the anti-rotation pin 169 into the bore after the rack 168 has been assembled into the implant 110, the engagement between the anti-rotation pin 169 and the flat side 173 along the back of the rack 168 prevents the rack 168 from rotating about its own longitudinal axis, which could cause the teeth 170 of the rack 168 to become disengaged from the teeth 164 of the pinions 162.

Figure 11:
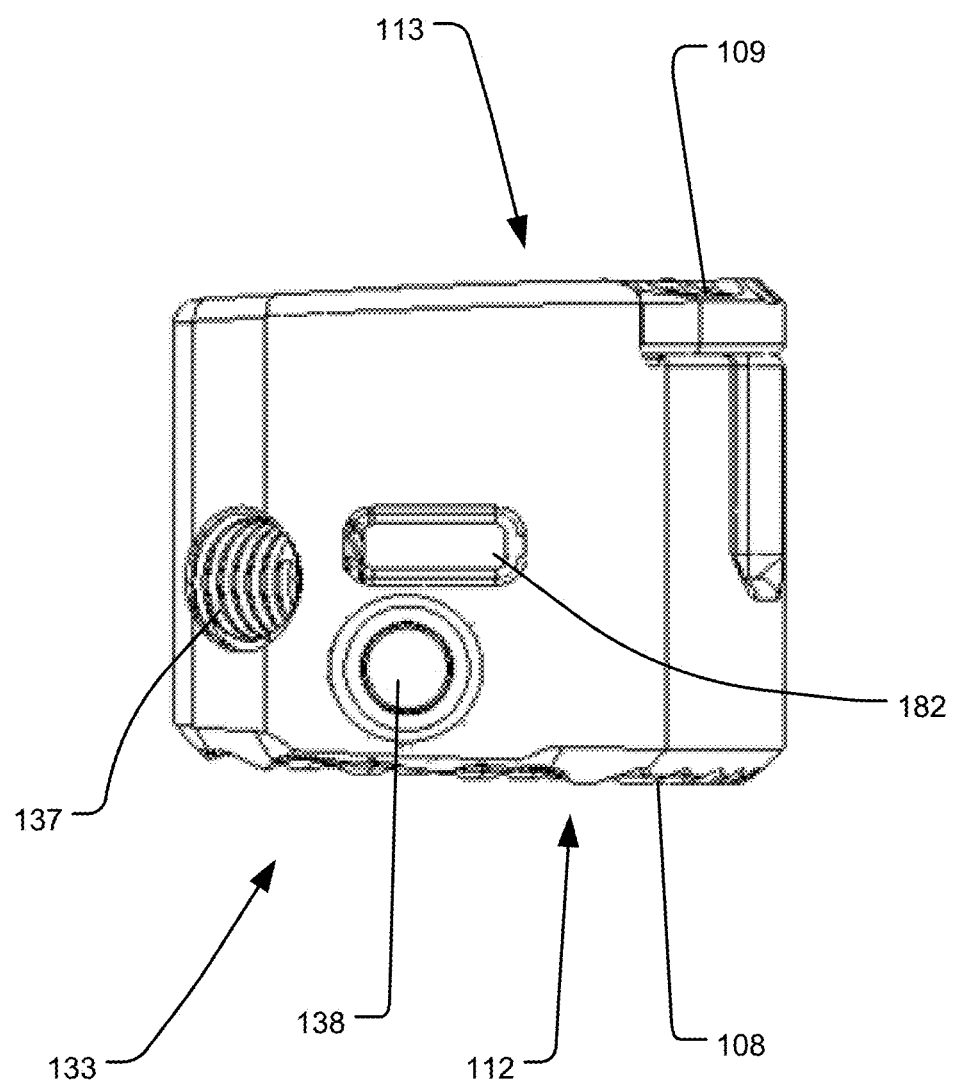
FIG. 11 is a rear elevation view of the embodiment of FIG. 8 in a contracted configuration.

As shown in FIG. 11, the top end surface 109 and the bottom end surface 108 of the implant 110 may be oriented at oblique angles to one another, which angles may be pre-defined to provide a desired lordosis angle to the vertebrae on either side of the disc space within which the implant 110 is positioned. Desirably, multiple implants 110 having different pre-defined lordosis angles may be made available to the surgeon, so that the surgeon can select an implant that is appropriate for the situation.

The outer configuration of the implants 10 and 110 illustrated in FIGS. 1-12B have a generally curved, kidney bean-like shape, and thus are consistent with the shapes of interbody implants used in TLIF techniques. The design of the locking system described above may also be employed in an implant 210 intended to be used in a PLIF technique, however, as illustrated in FIGS. 13A-17B. Unless otherwise noted, the components of the embodiment of FIGS. 13A-17B are similar to those of the embodiment illustrated in FIGS. 8-12B. Moreover, reference numerals in FIGS. 13A-17B similar to those in FIGS. 8-12B (i.e., increased by 100) are used to refer to analogous elements, and therefore such analogous elements may not be separately discussed below in connection with the embodiment of FIGS. 13A-17B.

Figure 15A:
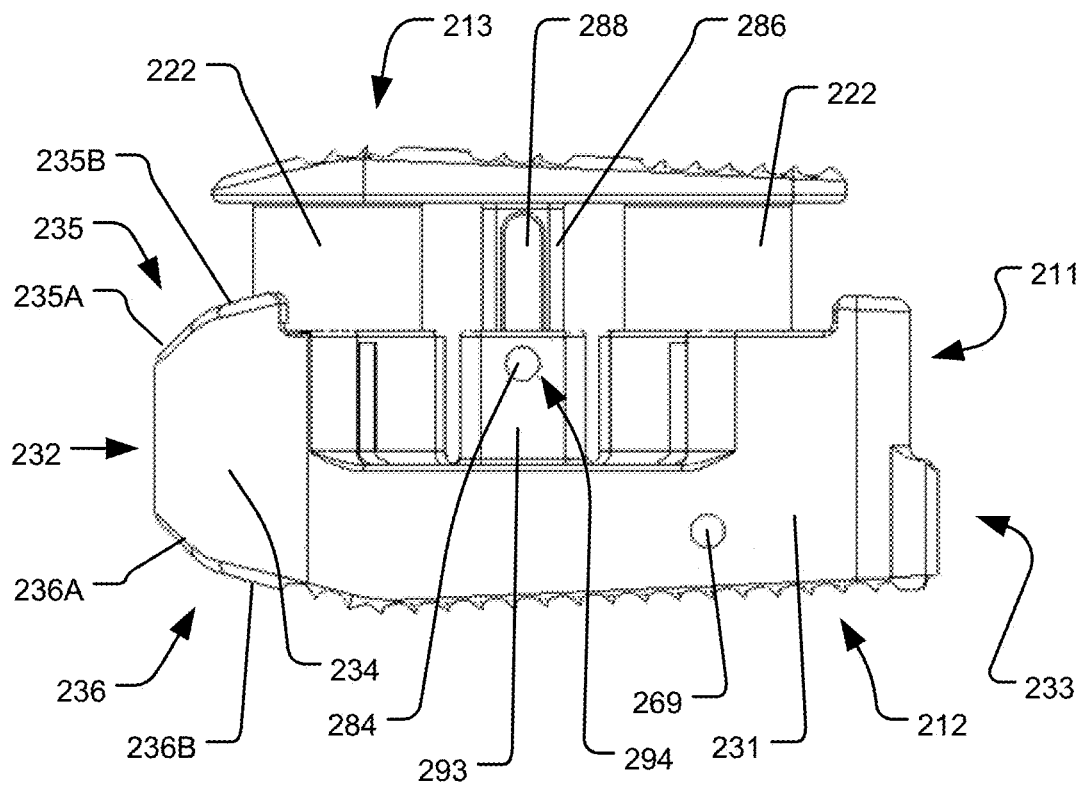
FIG. 15A is a side elevation view of the embodiment of FIG. 13A in an extended configuration.
Figure 15B:
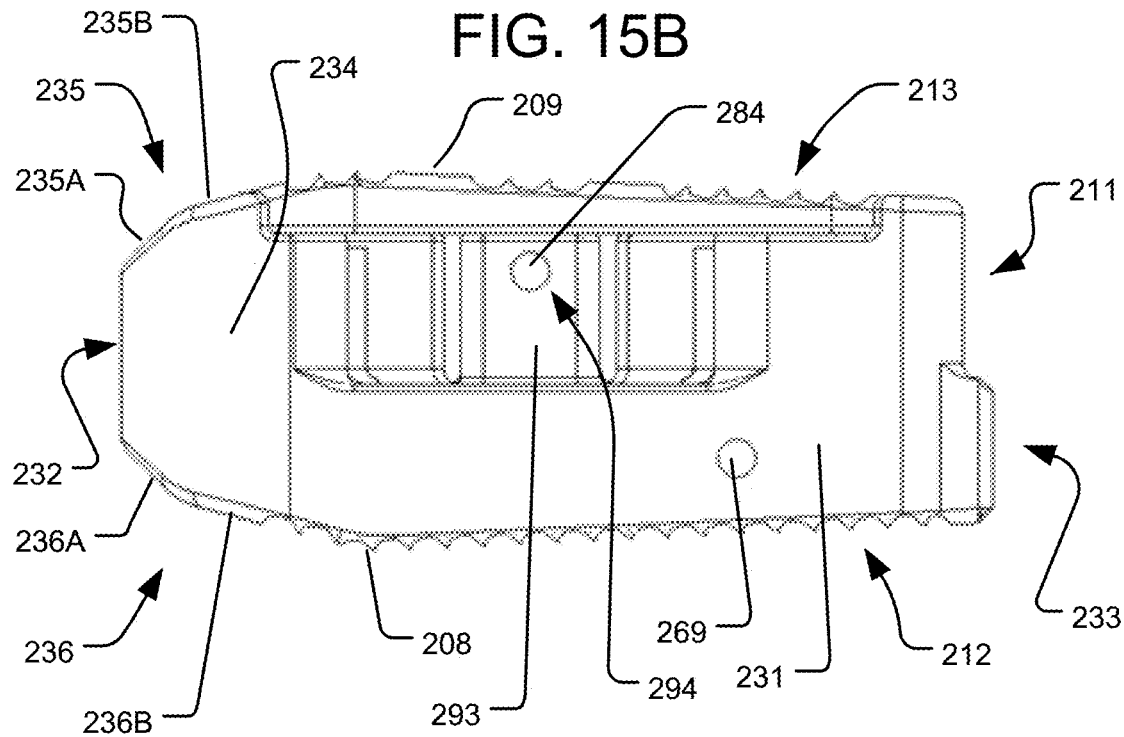
FIG. 15B is a side elevation view of the embodiment of FIG. 13A in a contracted configuration.
Figure 16:
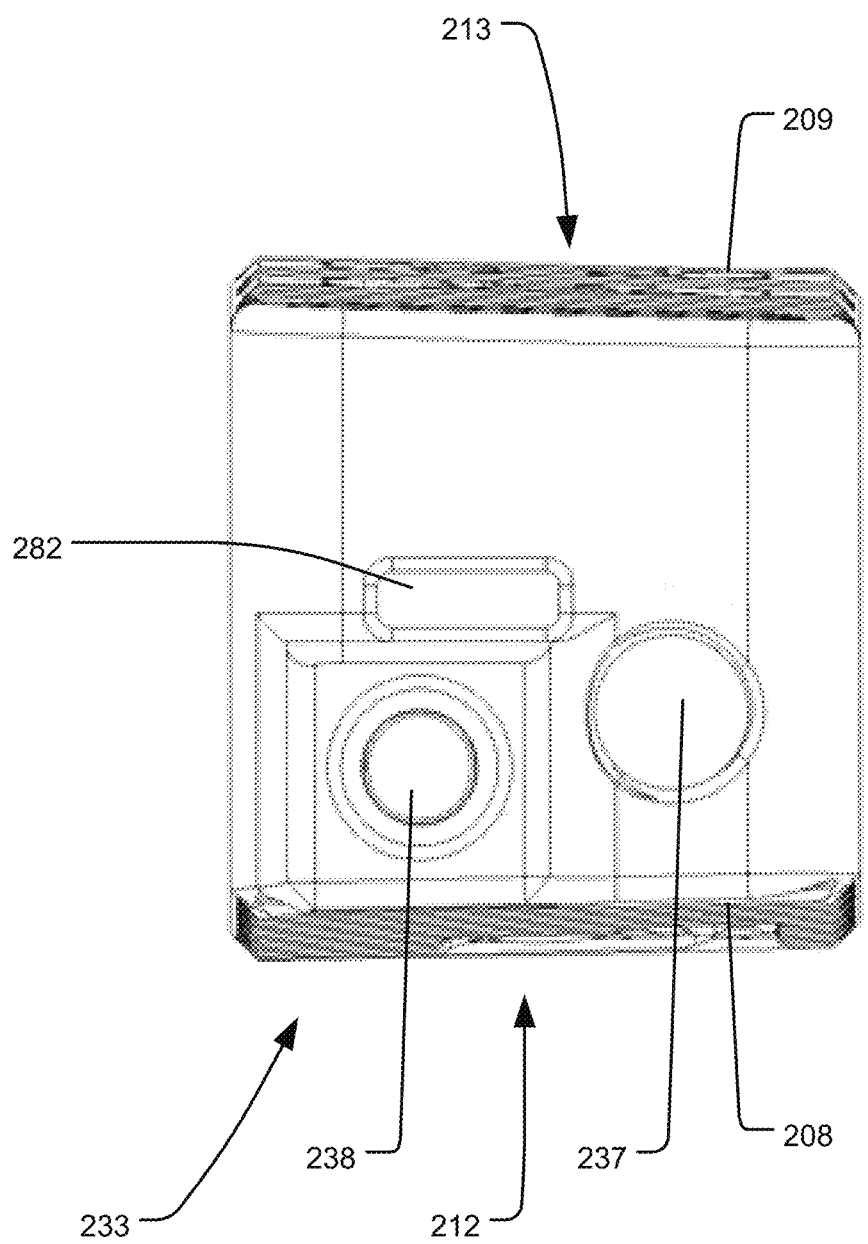
FIG. 16 is a rear elevation view of the embodiment of FIG. 13A in a contracted configuration.
Figure 17A:
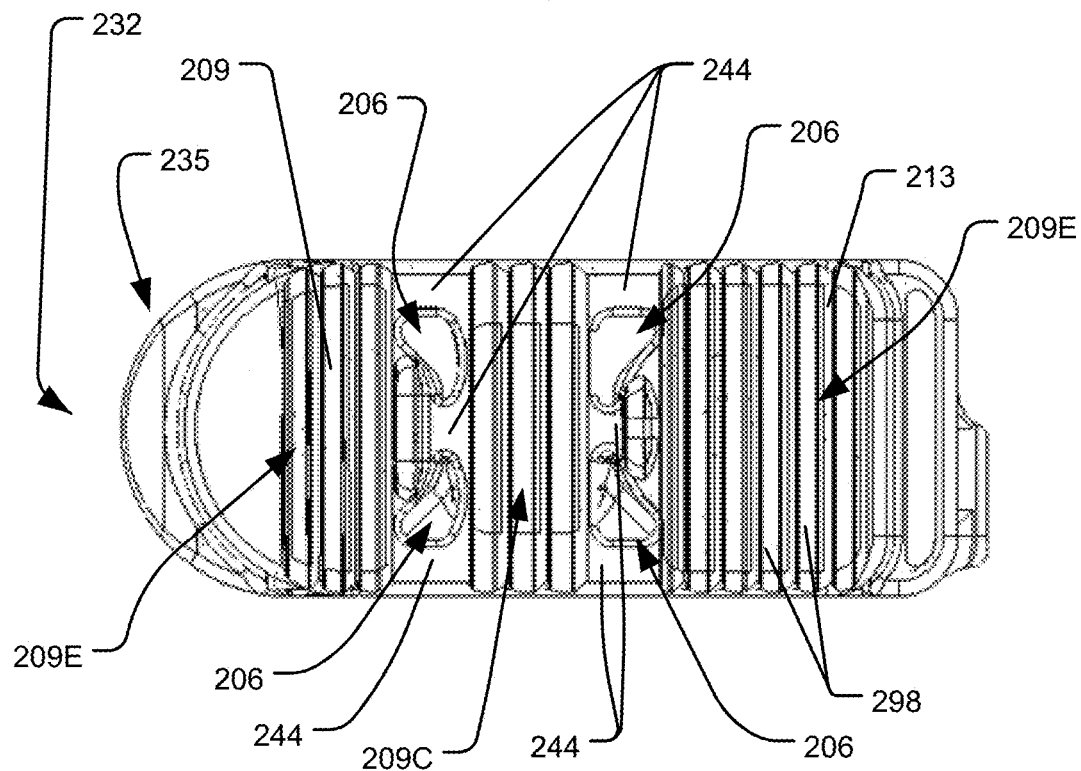
FIG. 17A is a top plan view of the embodiment of FIG. 13A.
Figure 17B:
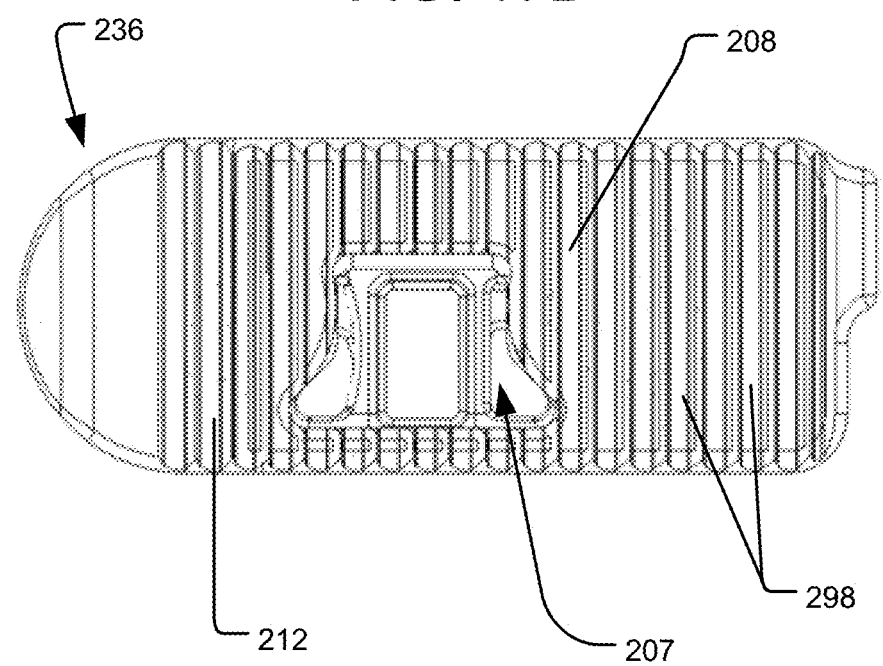
FIG. 17B is a bottom plan view of the embodiment of FIG. 13A.

One of the principal differences between the embodiment of the implant 210 in FIGS. 13A-17B and the embodiment of the implant 110 in FIGS. 8-12B is that the PLIF implant 210 has a generally straighter outer configuration along its central longitudinal axis than the implant 110 illustrated in FIGS. 8-12B. Like the TLIF implant 110 of FIGS. 8-12B, however, the PLIF implant 210 of FIGS. 13B-17B may also have its top end surface 209 oriented at an oblique angle to the bottom end surface 108 in the anterior/posterior direction (i.e., along the longitudinal axis of the implant 210), as shown in FIG. 15B. Moreover, like the TLIF implant 110, the PLIF implant 210 also be provided in a variety of such pre-defined lordosis angles. As shown in FIG. 16, the top and bottom end surfaces 209, 208 may also have a slight oblique angle with respect to one other in the medial/lateral direction (i.e., in the width direction of the implant 210).

As shown in FIG. 15B, the top and bottom tapered faces 235, 236 of the leading nose 232 of the PLIF implant 210 may be comprised of multiple facets having different angles. For example, the top tapered face 235 may include a distal top facet 235A having a steeper angle to the longitudinal axis of the implant 210 than a proximal top facet 235B. Similarly, the bottom tapered face 236 may include a distal bottom facet 236A having a steeper angle to the longitudinal axis than a proximal bottom facet 236B. Such multiple angles within the top and bottom tapered faces 235, 236 of the leading nose 232 desirably improve the non-traumatic insertability of the implant 210 by reducing the height of the implant at its distal-most end, while avoiding having the top and bottom tapered faces 235, 236 cut across the distal cylinder 216 of the implant.

As shown in the embodiments of FIGS. 8-17B, the top end surfaces and the bottom end surfaces of the implants may be provided with surface features so as to increase frictional engagement with the vertebrae above and below the implant, which may also provide additional areas for receiving bony ingrowth. For example, as shown in FIGS. 8 and 12A-B, the bottom and top end surfaces 108, 109 may be provided with a grid of pyramidal shaped protrusions 196. As shown in the embodiment of FIGS. 13A-B and 17A-B, the bottom and top end surfaces 208, 209 may be provided with linear ridges 298, which may extend along the width direction of the implant 10. Although the protrusions 196 are shown in connection with the TLIF implant 110 and the ridges 298 are shown in connection with the PLIF implant 210, each of those surface features could alternatively be used on the other type of implant. Moreover, although the above surface features are shown in connection with the embodiments of FIGS. 8-17B, such surface features could also be applied to the embodiment of FIGS. 1-7B.

Some or all of the components or portions of components of the implants 10, 110, 210 disclosed herein may be created by an additive manufacturing or 3D printing process, e.g., using Laser Rapid Manufacturing (LRM) technology. Additionally, or alternatively, some of the components or portions of components may be manufactured from a porous material, such as a porous metal. Such porous metal may be in the form of a porous, commercially-pure titanium matrix or a porous, titanium alloy (e.g., a Ti6Al4V alloy), such as those manufactured by Howmedica Osteonics Corp. under the trademark TRITANIUM®. Examples of additive manufacturing processes for creating some or all of the components of the implants 10, 110, 210 disclosed herein, including some such processes for creating porous materials, are disclosed in U.S. Pat. Nos. 7,537,664; 8,147,861; 8,350,186; 8,728,387; 8,992,703; 9,135,374; and 9,180,010, as well as U.S. Patent Application Publication No. 2006/0147332, all of which are hereby incorporated by reference herein as if fully set forth herein. In one example, the top end plate 13, 113, 213 and the bottom 12, 112, 212 of the housing 11, 111, 211 may include a porous titanium matrix formed via 3D printing, and then various features of the implant 10, 110, 210 may be further defined by machining of those components. For example, the surface features (e.g., pyramidal shaped protrusions 196 and linear ridges 298) may be defined in the porous matrix by machining the bottom end surface 8, 108, 208 and the top end surface 9, 109, 209. The porous material may also be supplemented by or replaced with solid or denser material in at least portions of the implant 10, 110, 210, however. For example, the tops of the pyramidal shaped protrusions 196 and/or linear ridges 298 may be formed from solid material, while the surrounding base portions that interconnect those features are formed from a porous matrix. Solid (non-porous) material may also be used in the portions of the implant 10, 110, 210 that enclose the hydraulic fluid. Solid material, which may be constructed with a smooth surface finish, may also be used along the interfaces between components that slide with respect to one another. Solid material may also be used in portions of the implant 10, 110, 210 where additional structural integrity is needed due to the loads that will be applied by the spine. For example, the periphery of the top end plate 13, 113, 213 may be constructed of solid material. In another example, the struts 44, 144, 244 and/or portions of the central portion 109C, 209C (e.g., one or more linear segments extending across the central portion along the longitudinal direction of the implant, so as to connect the struts) may be constructed of solid material, in order to increase the strength to the top end plate 13, 113, 213 and transfer the load applied by the projection 86, 186, 286 to the rest of the top end plate 13, 113, 213. In an alternative, portions of the implant 10, 110, 210 where additional structural integrity is needed may be constructed of a porous metal material, but the density of that material may be increased in those portions. Examples of implants having both solid and porous portions, as well as methods of creating the same, are disclosed in U.S. Provisional Patent Application No. 62/245,004, filed on Oct. 22, 2015, and U.S. Patent Application Publication No. 2016/0199193, the entire disclosures of which are hereby incorporated by reference herein as if fully set forth herein.

Although not illustrated in the embodiments of the invention discussed above, an implant 10, 110, 210 in accordance with embodiments of the present invention may include one or more bone graft infusion conduits within it for directing bone graft material therethrough, as disclosed in U.S. Pat. No. 9,028,550 ("the '550 Patent"), the entire disclosure of which is hereby incorporated by reference herein as if fully set forth herein. For example, the bone graft infusion conduit may communicate with one or more bone graft exit ports for dispersing bone graft material into and around the implant. In one example, as disclosed in the '550 Patent, at least one such bone graft exit port may communicate with the interior cavity 15, 115, 215, so as to fill the interior cavity of the implant 10, 110, 210 with bone graft material. The bone graft material may be supplied to the bone graft infusion conduit through a bone graft input port, which may be located at the engagement region 33, 133, 233 of the implant, so that the bone graft material may be supplied into the bone graft infusion conduit from the implant delivery tool.

Alternatively, or additionally, an implant 10, 110, 210 in accordance with embodiments of the present invention may include one or more manifolds, channels, or passages to permit flowable material to flow into or through the implant, as disclosed in U.S. Patent Application Publication No. 2016/0199190, the entire disclosure of which is hereby incorporated by reference herein as if fully set forth herein. For example, in an embodiment of the implant 10, 110, 210 having porous portions, as discussed above, one or more channels within the implant may communicate with one or more of such porous portions so as to supply the flowable material into and/or through those porous portions, as disclosed in the '697 Application. The flowable material may be supplied to the internal channels of the implant via an input port, which may be located at the engagement region 33, 133, 233 of the implant, so that the flowable material may be supplied by the implant delivery tool. One example of a flowable material for distribution via such internal channels is a flowable bone marrow aspirate.

Although the embodiments of the implant 10, 110, 210 disclosed above included pistons 22, 122, 222 and cylinders 16, 116, 216 driven by hydraulic pressure to expand the implant 10, 110, 210, other forms of extendable support elements may alternatively be used. For example, as disclosed in the '620 Patent, the implant 10, 110, 210 may be expanded by bellows, rotating cam lift mechanisms, rotating screw lift mechanisms, or other such devices. Moreover, the extendable support elements may be separately controllable (e.g., with separate hydraulic pressure channels), so that the extendable support elements can be extended to different vertical positions. In such embodiments, the top end plate 13, 113, 213 may instead take the form of separate plates associated with each extendable support element, or the top end plate 13, 113, 213 may be arranged to pivot with respect to the extendable support elements to accommodate their different vertical positions, as disclosed in the '620 Patent. In other alternative embodiments in accordance with the present invention, rather than being positioned within the pistons and cylinders, the upper and lower lock supports can be positioned around the pistons and cylinders, as in certain embodiments disclosed in the '620 Patent.

Although the embodiments disclosed herein illustrate implants 10, 110, 210 in which a pair of extendable support elements (e.g., two pistons with two corresponding cylinders) as well as a pair of locking elements (e.g., two upper lock supports 17, 117, 217 with two corresponding lower lock supports 20, 120, 220) are provided, alternative embodiments may only include one of each such component. Still further embodiments may include more than two of each component.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A spinal implant for placement between first and second vertebral bodies, comprising: a first member having a first surface for engaging a first vertebral body; a second member having a second surface for engaging a second vertebral body; at least one extendable support element having a contracted configuration to facilitate deployment of the implant between the first and second vertebral bodies, and the extendable support element having at least one extended configuration to extend the first and second members away from one another so that the first and second surfaces are positioned further apart from one another than in the contracted configuration; and a locking system comprising at least one locking element movable between a locked configuration and an unlocked configuration, wherein the locking element prevents movement of the extendable support element towards the contracted configuration when the locking element is in the locked configuration, and the locking element permits movement of the extendable support element towards the contracted configuration when the locking element is in the unlocked configuration; wherein the locking element includes a pinion, such that movement of the locking element between the locked and unlocked configuration is actuated by rotation of the pinion; further comprising a linear rack extending along an axis, the linear rack being linearly translatable along the axis to induce rotation of the pinion.

2. The spinal implant of claim 1, wherein the linear rack moves linearly within a channel, the channel supplying a fluid for extending the extendable support element.

3. The spinal implant of claim 1, wherein the linear rack is biased so as to move the locking element towards the locked configuration.

4. The spinal element of claim 3, wherein the linear rack is biased by a linear spring.

5. The spinal implant of claim 1, wherein the locking system further comprises a second locking element having a second pinion, the second locking element being movable between a locked configuration and an unlocked configuration, wherein the second locking element prevents movement of a second extendable support element towards the contracted configuration when the second locking element is in the locked configuration, and the second locking element permits movement of the second extendable support element towards the contracted configuration when the second locking element is in the unlocked configuration; wherein movement of the second locking element between the locked and unlocked configuration is actuated by rotation of the second pinion; and wherein the linear rack is engaged with the pinion and the second pinion for simultaneously rotating the pinion and the second pinion.

6. The spinal element of claim 1, wherein the extendable support element is configured to be extended by a fluid.

7. The spinal element of claim 1, wherein the extendable support element includes a piston slidably received within a cylinder.

8. The spinal element of claim 7, wherein the at least one locking element is received within the cylinder.

9. The spinal element of claim 1, wherein the locking system comprises a plurality of inter-engaging locking elements, including an upper lock support member and a lower lock support member; wherein the upper lock support member has a multi-stepped support surface, and the lower lock support system has a multi-stepped support surface configured to move into engagement with the multi-stepped support surface of the upper lock support member in the locked configuration; and wherein the at least one locking element is one of the upper and lower lock support members.

10. The spinal implant of claim 9, wherein the at least one locking element is the lower lock support member, the lower lock support member being rotatable relative to the upper lock support member between the locked configuration and the unlocked configuration in response to rotation of the pinion.

11. The spinal implant of claim 10, wherein the lower lock support member is rotatable relative to the upper lock support member about an axle rigidly connected to one of the first and second members.

12. The spinal implant of claim 10, wherein the extendable support element includes a piston slidably received within a cylinder; and wherein the upper lock support member is disposed within the piston and the lower lock support member is rotatably received within the cylinder.

13. The spinal implant of claim 1, wherein one of the first and second members defines a slot extending along an extension direction, and the wherein the other of the first and second members includes a projection received within the slot, the projection preventing further extension of the first and second members away from one another when the projection abuts an end of the slot.

14. The spinal implant of claim 13, wherein the at least one extendable support element comprises a first extendable support element and a second extendable support element, and wherein the projection and the slot are positioned between the first and second extendable support elements.

15. The spinal implant of claim 1, wherein at least one of the first surface and the second surface is constructed of a porous metal.

16. The spinal implant of claim 1, wherein the implant has a curved, kidney bean-like shape.

17. The spinal implant of claim 1, wherein the implant has a straight shape along its central longitudinal axis.

\* \* \* \* \*